United States Patent
Roovers et al.

(10) Patent No.: US 12,428,493 B2
(45) Date of Patent: Sep. 30, 2025

(54) ANTIBODIES THAT BIND PSMA AND GAMMA-DELTA T CELL RECEPTORS

(71) Applicant: LAVA THERAPEUTICS N.V., Utrecht (NL)

(72) Inventors: Robertus Cornelis Roovers, Utrecht (NL); Johannes Jelle Van Der Vliet, Amsterdam (NL); Lisa Anna King, Amsterdam (NL); Paul Willem Henri Ida Parren, Utrecht (NL); Victoria Iglesias Guimarais, Utrecht (NL); David Lutje Hulsik, Utrecht (NL); Peter Alexander Gerardus Maria Machielsen, Utrecht (NL)

(73) Assignee: LAVA THERAPEUTICS N.V., Utrecht (NL)

( * ) Notice: Subject to any disclaimer, the term of this patent is extended or adjusted under 35 U.S.C. 154(b) by 0 days.

(21) Appl. No.: 18/656,081

(22) Filed: May 6, 2024

(65) Prior Publication Data
US 2024/0317888 A1   Sep. 26, 2024

Related U.S. Application Data

(63) Continuation of application No. 18/014,457, filed as application No. PCT/EP2021/068960 on Jul. 8, 2021.

(30) Foreign Application Priority Data

Jul. 8, 2020 (EP) ..................................... 20184800

(51) Int. Cl.
| | | |
|---|---|---|
| C07K 16/00 | (2006.01) | |
| A61K 39/00 | (2006.01) | |
| A61P 35/00 | (2006.01) | |
| C07K 16/28 | (2006.01) | |
| C07K 16/30 | (2006.01) | |
| C07K 16/46 | (2006.01) | |

(52) U.S. Cl.
CPC .. *C07K 16/3069* (2013.01); *A61K 39/001195* (2018.08); *A61P 35/00* (2018.01); *C07K 16/2809* (2013.01); *C07K 16/468* (2013.01); *C07K 2317/31* (2013.01); *C07K 2317/526* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,723,309 A | 3/1998 | Bonneville | |
| 6,737,398 B1 | 5/2004 | Gelfand et al. | |
| 7,582,300 B2 | 9/2009 | Gelfand et al. | |
| 7,728,114 B2 | 6/2010 | Mach et al. | |
| 7,811,564 B2 | 10/2010 | Cuello et al. | |
| 7,875,278 B2 | 1/2011 | Cardarelli et al. | |
| 8,114,965 B2 | 2/2012 | Maddon et al. | |
| 8,153,426 B2 | 4/2012 | Moser et al. | |
| 8,178,098 B2 | 5/2012 | Lahn et al. | |
| 8,338,173 B2 | 12/2012 | Moser et al. | |
| 8,461,308 B2 | 6/2013 | Cardarelli et al. | |
| 8,470,330 B2 | 6/2013 | Maddon et al. | |
| 9,695,248 B2 | 7/2017 | Maddon et al. | |
| 9,708,412 B2 | 7/2017 | Baeuerle et al. | |
| 10,106,623 B2 | 10/2018 | Uhlin et al. | |
| 10,501,540 B2 | 12/2019 | Van Der Vliet et al. | |
| 10,758,625 B2 | 9/2020 | Yu et al. | |
| 10,844,134 B2 | 11/2020 | Baeuerle et al. | |
| 10,849,973 B2 | 12/2020 | DuBridge et al. | |
| 10,954,311 B2 | 3/2021 | Baeuerle et al. | |
| 11,000,603 B2 | 5/2021 | Yu et al. | |
| 11,384,145 B2 | 7/2022 | Van Der Vliet et al. | |
| 2019/0263908 A1 | 8/2019 | Van Der Vliet et al. | |
| 2021/0095047 A1 | 4/2021 | Baeuerle et al. | |
| 2021/0100902 A1 | 4/2021 | DuBridge et al. | |
| 2021/0284730 A1 | 9/2021 | Ganesan et al. | |
| 2022/0098301 A1 | 3/2022 | Van Der Vliet et al. | |
| 2023/0212290 A1 | 7/2023 | Van Der Vliet | |
| 2023/0272110 A1 | 8/2023 | Roovers et al. | |

FOREIGN PATENT DOCUMENTS

| | | |
|---|---|---|
| EP | 1229790 A1 | 8/2002 |
| EP | 1778836 B1 | 8/2010 |
| EP | 2360169 A2 | 8/2011 |
| EP | 1587837 B1 | 6/2012 |
| EP | 3297672 A1 | 3/2018 |
| EP | 3105252 B1 | 7/2019 |
| EP | 3544629 A1 | 10/2019 |
| EP | 3544997 A1 | 10/2019 |
| EP | 4118121 A1 | 1/2023 |

(Continued)

OTHER PUBLICATIONS

Brinkmann, U. et al. The Making of Bispecific Antibodies. MAbs 9.2 (2017): 182-212 (Year: 2017).*
Engelberts, Patrick J et al. DuoBody-CD3xCD20 Induces Potent T-Cell-Mediated Killing of Malignant B Cells in Preclinical Models and Provides Opportunities for Subcutaneous Dosing. EBioMedicine 52 (2020): 102625 (Year: 2020).*
Paul, S. et al. Regulatory and Effector Functions of Gamma Delta T Cells and Their Therapeutic Potential in Adoptive Cellular Therapy for Cancer. International journal of cancer 139.5 (2016): 976-985 (Year: 2016).*

(Continued)

*Primary Examiner* — Janet L Epps-Smith
*Assistant Examiner* — Estella M. Gustilo
(74) *Attorney, Agent, or Firm* — COOLEY LLP

(57) ABSTRACT

The present invention relates to antibodies capable of binding human PSMA and capable of binding a human Vγ9Vδ2 T cell receptor. The invention further relates to pharmaceutical compositions comprising the antibodies of the invention and to uses of the antibodies of the invention for medical treatment.

8 Claims, 18 Drawing Sheets
Specification includes a Sequence Listing.

(56) References Cited

FOREIGN PATENT DOCUMENTS

| | | |
|---|---|---|
| WO | WO-0122816 A1 | 4/2001 |
| WO | WO-02080967 A1 | 10/2002 |
| WO | WO-03034903 A2 | 5/2003 |
| WO | WO-03068821 A2 | 8/2003 |
| WO | WO-03080672 A1 | 10/2003 |
| WO | WO-2004062551 A2 | 7/2004 |
| WO | WO-2004067570 A2 | 8/2004 |
| WO | WO-2005042029 A2 | 5/2005 |
| WO | WO-2005046711 A2 | 5/2005 |
| WO | WO-2006017954 A1 | 2/2006 |
| WO | WO-2006089230 A2 | 8/2006 |
| WO | WO-2006089231 A2 | 8/2006 |
| WO | WO-2006125481 A1 | 11/2006 |
| WO | WO-2007038658 A2 | 4/2007 |
| WO | WO-2008006895 A2 | 1/2008 |
| WO | WO-2009046294 A2 | 4/2009 |
| WO | WO-2009130575 A2 | 10/2009 |
| WO | WO-2010118522 A1 | 10/2010 |
| WO | WO-2012145714 A2 | 10/2012 |
| WO | WO-2013110531 A1 | 8/2013 |
| WO | WO-2013138400 A1 | 9/2013 |
| WO | WO-2013147606 A1 | 10/2013 |
| WO | WO-2013173820 A2 | 11/2013 |
| WO | WO-2013174403 A1 | 11/2013 |
| WO | WO-2013174404 A1 | 11/2013 |
| WO | WO-2013174509 A1 | 11/2013 |
| WO | WO-2013174510 A1 | 11/2013 |
| WO | WO-2014012479 A1 | 1/2014 |
| WO | WO-2014055097 A1 | 4/2014 |
| WO | WO-2014127785 A1 | 8/2014 |
| WO | WO-2014127906 A1 | 8/2014 |
| WO | WO-2015044386 A1 | 4/2015 |
| WO | WO-2015121383 A1 | 8/2015 |
| WO | WO-2015156673 A1 | 10/2015 |
| WO | WO-2016081518 A2 | 5/2016 |
| WO | WO-2016145139 A1 | 9/2016 |
| WO | WO-2016165302 A1 | 10/2016 |
| WO | WO-2016179518 A2 | 11/2016 |
| WO | WO-2016180969 A1 | 11/2016 |
| WO | WO-2016187594 A1 | 11/2016 |
| WO | WO-2017023761 A1 | 2/2017 |
| WO | WO-2017053856 A1 | 3/2017 |
| WO | WO-2017121905 A1 | 7/2017 |
| WO | WO-2017122017 A1 | 7/2017 |
| WO | WO-2017122018 A1 | 7/2017 |
| WO | WO-2017122019 A1 | 7/2017 |
| WO | WO-2017180713 A1 | 10/2017 |
| WO | WO-2017185662 A1 | 11/2017 |
| WO | WO-2018023111 A1 | 2/2018 |
| WO | WO-2018071777 A1 | 4/2018 |
| WO | WO 2018/098354 A1 * | 5/2018 | ....... A61K 39/39558 |
| WO | WO-2018098356 A1 | 5/2018 |
| WO | WO-2018140831 A2 | 8/2018 |
| WO | WO-2018229163 A1 | 12/2018 |
| WO | WO-2019055841 A1 | 3/2019 |
| WO | WO-2019070424 A1 | 4/2019 |
| WO | WO-2019195535 A1 | 10/2019 |
| WO | WO-2019224718 A2 | 11/2019 |
| WO | WO-2019245991 A1 | 12/2019 |
| WO | WO 2019246514 A * | 12/2019 | ......... C07K 16/2818 |
| WO | WO-2020010250 A2 | 1/2020 |
| WO | WO 2020/060406 A1 * | 3/2020 | ......... C07K 16/2833 |
| WO | WO-2020060405 A1 | 3/2020 |
| WO | WO-2020159368 A1 | 8/2020 |
| WO | WO-2020172596 A1 | 8/2020 |
| WO | WO-2020227457 A1 | 11/2020 |
| WO | WO-2021032960 A1 | 2/2021 |
| WO | WO-2021032961 A1 | 2/2021 |
| WO | WO-2021032963 A1 | 2/2021 |
| WO | WO-2021052995 A1 | 3/2021 |
| WO | WO-2021173896 A1 | 9/2021 |
| WO | WO-2021183845 A1 | 9/2021 |
| WO | WO-2021231434 A1 | 11/2021 |
| WO | WO-2022093888 A1 | 5/2022 |
| WO | WO-2022122973 A1 | 6/2022 |
| WO | WO-2022192225 A1 | 9/2022 |

OTHER PUBLICATIONS

Allison et al., "Structure of a human γδ T-cell antigen receptor", Nature. Jun. 14, 2001, vol. 411, 820-824.

Beckman Coulter, Inc., "TCR Vgamma 9", https://www.beckmancoulter.com/wsrportal/page/itemDetails?itemNumber=IM1463#2/10//0/25/1 /0/asc/2/IM14631//0/1//0/, retrieved on Sep. 26, 2014, 1 page.

Bedouelle et al., "Diversity and junction residues as hotspots of binding energy in an antibody neutralizing the dengue virus", FEBS J. (2006); 273(1):34-46.

Brown, M. et al., "Tolerance to Single, but Not Multiple, Amino Acid Replacements in Antibody VH CDR2: A Means of Minimizing B Cell Wastage from Somatic Hypermutation", The Journal of Immunology (1996); 156(9):3285-3291.

Chatalic et al. "A Novel $^{111}$In-Labeled Anti-Prostate-Specific Membrane Antigen Nanobody for Targeted SPECT/CT Imaging of Prostate Cancer", J Nucl Med. Jul. 2015;56(7):1094-1099.

Colman, P.M. (1994) "Effects of amino acid sequence changes on antibody-antigen interactions" Research in Immunology, 145(1):33-36.

Communication Pursuant to Article 94(3) EPC for European Application No. 15 722 781.0, dated Feb. 7, 2018, 5 pages.

De Bruin, et al., "A Bispecific Nanobody Approach to Leverage the Potent and Widely Applicable Tumor Cytolytic Capacity of Vγ9Vδ2-T Cells" Oncoimmunology, Sep. 11, 2017, pp. 1-38.

De Bruin et al., "Highly specific and potently activating Vγ9Vδ2-T cell specific nanobodies for diagnostic and therapeutic applications" Clinical Immunology, Aug. 2016, pp. 128-138.

De Bruin et al., "Prevention of Vγ9Vδ2 T Cell Activation by a Vγ9Vδ2 TCR Nanobody", J Immunol., Jan. 1, 2017;198(1):308-317.

Dondelinger et al., "Understanding the Significance and Implications of Antibody Numbering and Antigen-Binding Surface/Residue Definition," Frontiers in Immunology, Oct. 2018, 9: 2278, 15 pages.

Edwards, B.M. et al., "The Remarkable Flexibility of the Human Antibody Repertoire; Isolation of Over One Thousand Different Antibodies to a Single Protein, BLyS," Journal of Molecular Biology, Nov. 14, 2003, 334(1), pp. 103-118.

Ferrini et al., "Re-targeting of human lymphocytes expressing the T-cell receptor gamma/delta to ovarian carcinoma cells by the use of bispecific monoclonal antibodies", Int. J. Cancer: 44, 245-250 (1989).

Ferrini et al., "Monoclonal antibodies which react with the T cell receptor y/o recognize different subsets of CD3+WT31-T lymphocytes", Eur. J. Immunol. 1989. 19:57-61.

Haberkorn et al., "New Strategies in Prostate Cancer: Prostate-Specific Membrane Antigen (PSMA) Ligands for Diagnosis and Therapy", Clin Cancer Res., Jan. 1, 2016;22(1):9-15.

Harlow et al., "Antibody Response", Chapter 4, and "Immunizations", Chapter 5, Antibodies, A Laboratory Manual, Cold Spring Harbor Laboratory, 1988, pp. 37-47, 55-59.

Hernandez-Hoyos, G., et al., "MOR209/ES414, a Novel Bispecific Antibody Targeting PSMA for the Treatment of Metastatic Castration-Resistant Prostate Cancer," Molecular Cancer Therapeutics, Sep. 2016, vol. 15(9), pp. 2155-2165.

International Search Report and Written Opinion, PCT/EP2021/068960, Nov. 3, 2021, 13 pages.

International Search Report and Written Opinion, PCT/EP2021/085079, Mar. 11, 2022, 13 pages.

International Search Report issued to International Application No. PCT/NL2015/050235, mailed Jul. 10, 2015, 6 pages.

Kabelitz et al., "Cancer immunotherapy with [gamma][delta] T cells: many paths ahead of us", Cell Mol Immunol., Sep. 2020;17(9):925-939. Epub Jul. 22, 2020.

Langerak, et al., "Immunophenotypic and immunogenotypic characteristics of TCRyo+ T cell acute lymphoblastic leukemia", Leukemia (1999); 13, 206-214.

(56) References Cited

OTHER PUBLICATIONS

Lloyd, C., et al., "Modelling the human immune response: performance of a 1011 human antibody repertoire against a broad panel of therapeutically relevant antigens", Protein Engineering, Design and Selection, Mar. 2009, 22(3), pp. 159-168.

Miossec et al., "Further analysis of the T cell receptor gamma/delta+ peripheral lymphocyte subset. The V delta 1 gene segment is expressed with either C alpha or C delta", J. Exp. Med., vol. 171, Apr. 1990, 1171-1188.

Muyldermans, S. (2013) "Nanobodies: Natural Single-Domain Antibodies". Annu Rev Biochem, 82:775-797.

Muyldermans, S., "Single domain camel antibodies: current status," Rev. Mol. Biotechnol. 74:277-302, 2001.

Oberg et al., "Novel Bispecific Antibodies Increase γδ T-Cell Cytotoxicity against Pancreatic Cancer Cells", Cancer Res; 74(5); 1349-60, 2014.

PE Anti-human TCR Vδ2 Antibody (BioLegend). 2012, 3 pages, URL at https://www.biolegend.com/fr-ch/products/pe-anti-human-tcr-vdelta2-antibody-4571?GroupID=BLG13659.

Roovers et al., "Efficient inhibition of EGFR signaling and of tumour growth by antagonistic anti-EFGR Nanobodies," Cancer Immunol Immunother, Mar. 2007; 56(3): 303-17.

Rudikoff, S., et al., "Single amino acid substitution altering antigen-binding specificity", Proceedings of the National Academy of Sciences (1982); 79(6): 1979-1983.

Saerens et al., "Identification of a Universal VHH Framework to Graft Non-canonical Antigen-binding Loops of Camel Single-domain Antibodies", J. Mol. Biol. (2005) 352, 597-607.

Silva-Santos, et al., "[gamma][delta] T cells: pleiotropic immune effectors with therapeutic potential in cancer", Nat Rev Cancer. Jul. 2019;19(7):392-404.

Smolarek et al., Variable fragments of heavy chain antibodies (VHHs): a new magic bullet molecule of medicine?*, Postepy Hig Med Dosw (online), 2012; 66: 348-358.

Szereday, L. et al., "γ/δ T cell subsets in patients with active *Mycobacterium tuberculosis* infection and tuberculin anergy", Clin Exp Immunol, Feb. 2003; 131(2):287-291.

Tamura, M. et al., "Structural correlates of an anticarcinoma antibody: identification of specificity-determining residues (SDRs) and development of a minimally immunogenic antibody variant by retention of SDRs only," J. Immunol., 2000, vol. 164, No. 3, pp. 1432-1441.

Vajdos, F. F., et al., "Comprehensive functional maps of the antigen-binding site of an anti-ErbB2 antibody obtained with shotgun scanning mutagenesis", Journal of Molecular Biology (2002); 320(2): 415-428.

Vecchi, Maurizio, et al., Increased Jejunal Intraepithelial Lymphocytes Bearing γ/σ T-Cell Receptor in Dermatitis Herpetiformis, Gastroenterology, 1992; 102:1499-1505.

Viale et al., "TCR gamma/delta positive lymphocytes after allogeneic bone marrow transplantation", Bone Marrow Transplantation 1992, 10:249-253.

Vincke, C. et al., "General strategy to humanize a camelid single-domain antibody and identification of a universal humanized nanobody scaffold", J Biol Chem. (2009); 284(5):3273-3284.

Written Opinion of the International Searching Authority for International Application No. PCT/NL2015/050235, mailed Jul. 10, 2015, 8 pages.

Wrobel, P., et al., "Lysis of a Broad Range of Epithelial Tumour Cells by Human gamma delta T Cells: Involvement of NKG2D ligands and T-cell Receptor-versus NKG2D-dependent Recognition", Scandinavian Journal of Immunology, 2007, 66, 320-328.

Zabetakis et al., "Contributions of the Complementarity Determining Regions to the Thermal Stability of a Single-Domain Antibody", PLOS ONE, Oct. 2013, vol. 8, Issue 10, e77678, 1-7.

Zhou et al., "Anti-γδ TCR antibody-expanded γδ T cells: a better choice for the adoptive immunotherapy of lymphoid malignancies", Cellular & Molecular Immunology (2012) 9, 34-44.

* cited by examiner

Fig. 1

| LV 1044 | EVQLVESGGGLVQPGGSLTLSCAASRFMISEYSMHWVRQAPGKGLEWVSTINPAGTTDYAESVKGRFTISRDNAKNTLYLQMNSLKPEDTAVYYCDGYGYRGQGTQVTVSS |
| LV 1050 | EVQLVESGGGLVQPGGSLRLSCAASRFMISEYSMHWVRQAPGKGLEWVSTINPAGTTDYADSVKGRFTISRDNAKNTLYLQMNSLRAEDTAVYYCDGYGYRGQGTQVTVSS |
| LV 1051 | EVQLVESGGGSVQPGGSLRLSCAASRFMISEYSMHWVRQAPGKGLEWVSTINPAGTTDYADSVKGRFTISRDNAKNTLYLQMNSLRAEDTAVYYCDGYGYRGLGTQVTVSS |

Fig. 3
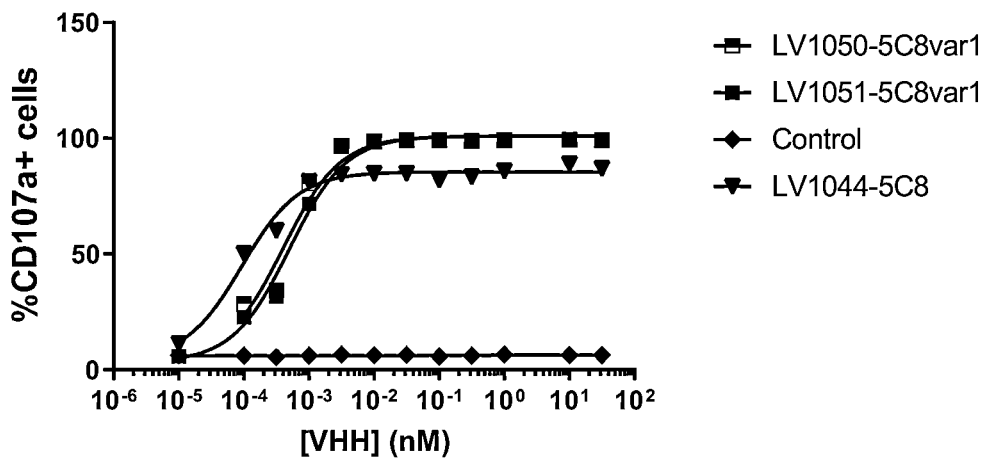
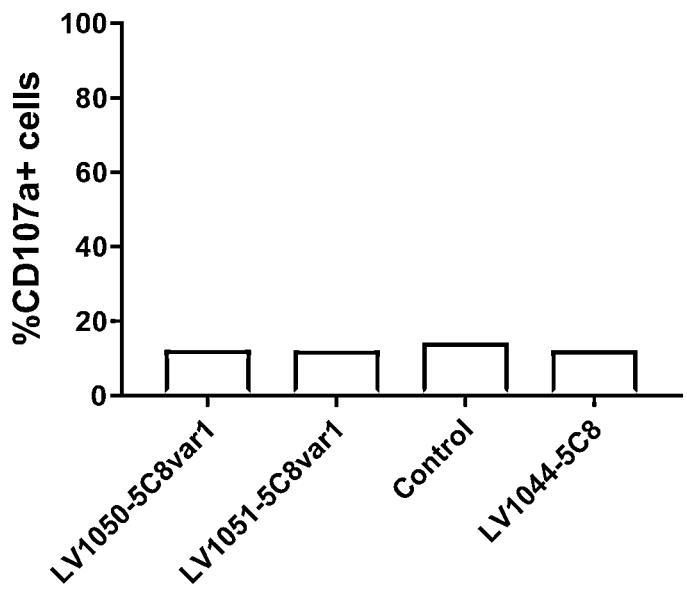

Fig. 5
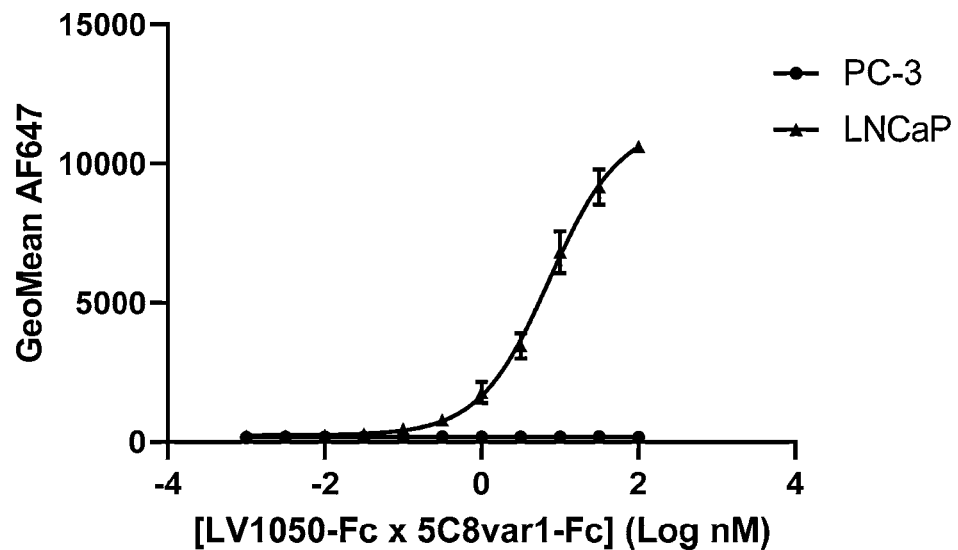
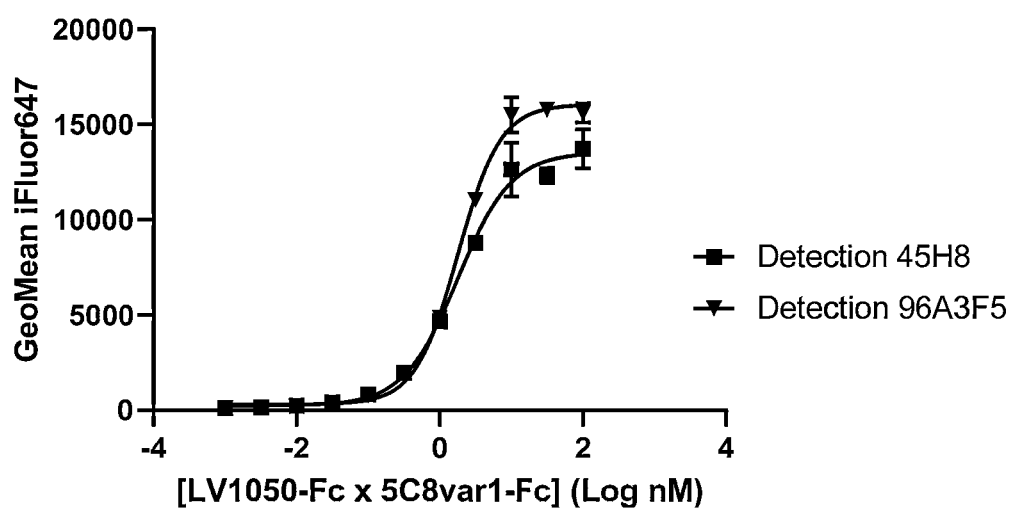

Fig. 6
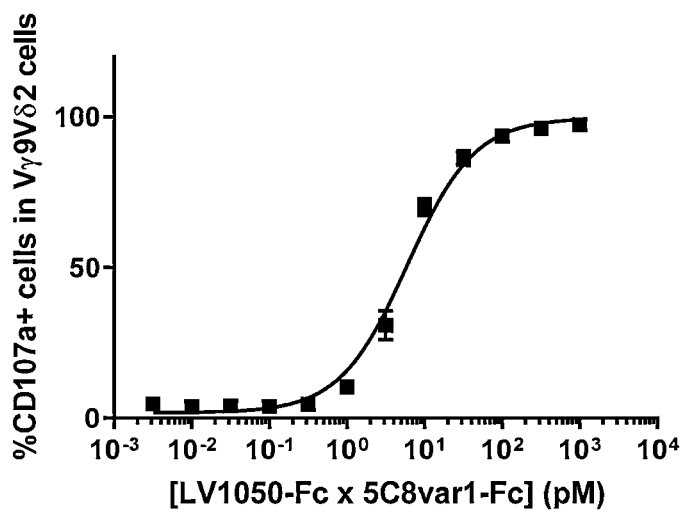
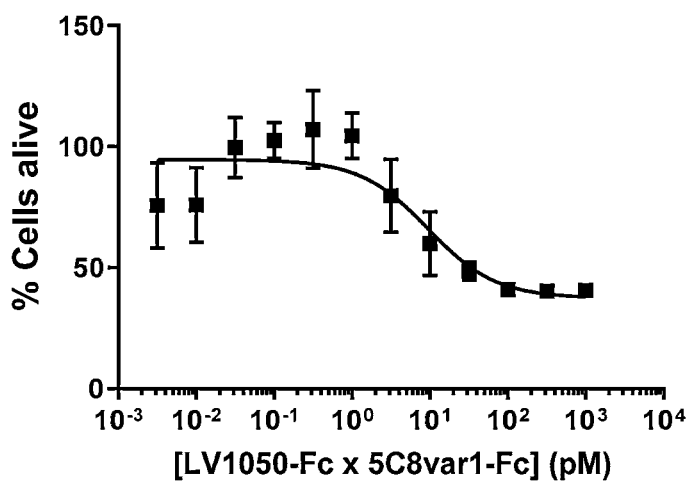

Fig. 7
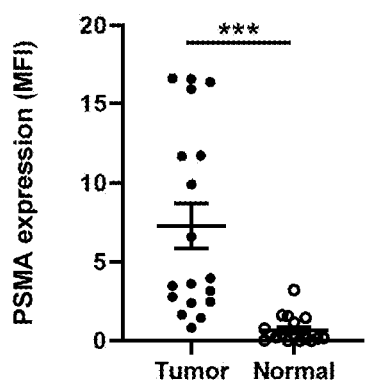
Tumor: n = 18, mean +/- S.E.M.
Normal: n = 17, mean +/- S.E.M.
*** p <0.001
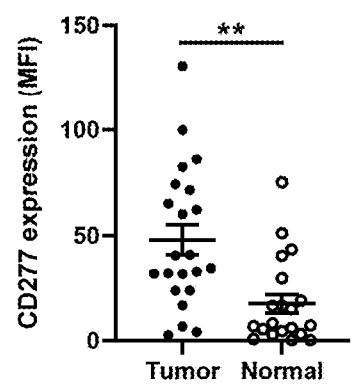
Tumor: n = 22, mean +/- S.E.M.
Normal: n = 20, mean +/- S.E.M.
**p <0.01
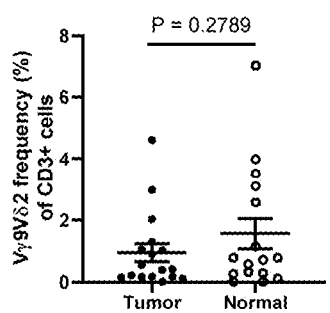
Tumor: n = 17, mean +/- S.E.M.
Normal: n = 16, mean +/- S.E.M.

Fig. 8
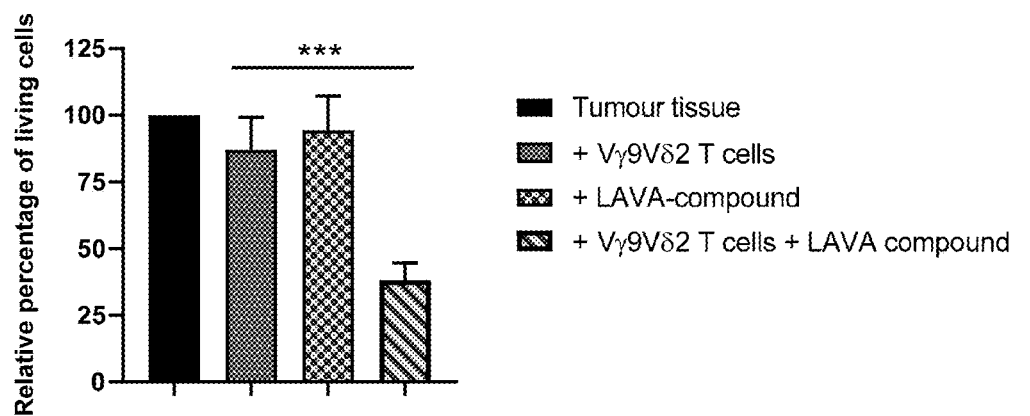
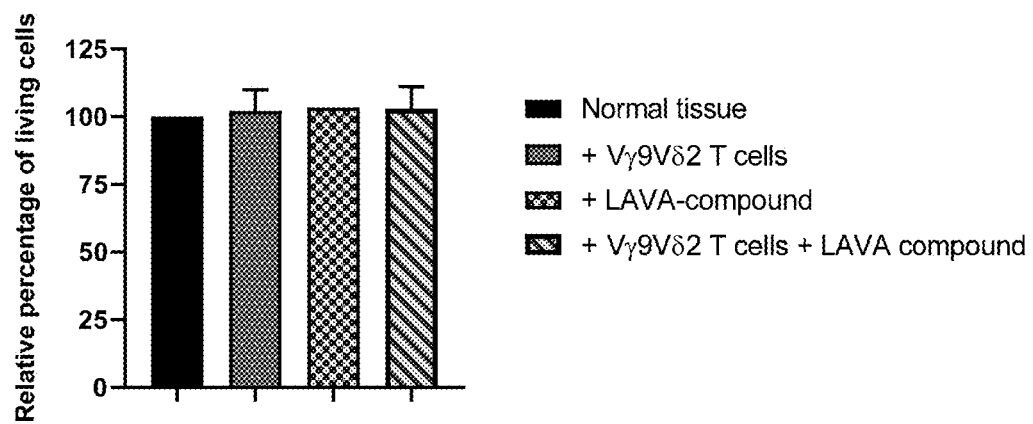

Fig. 12
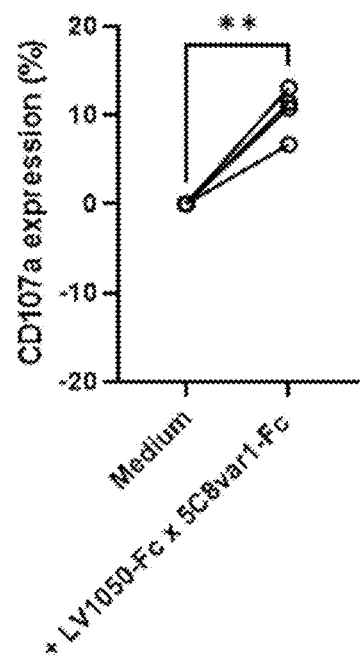
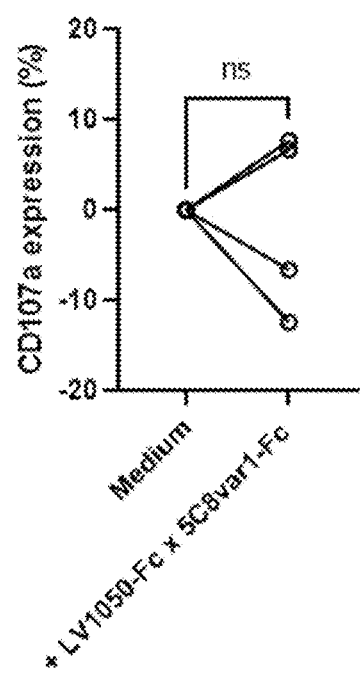

Fig. 13
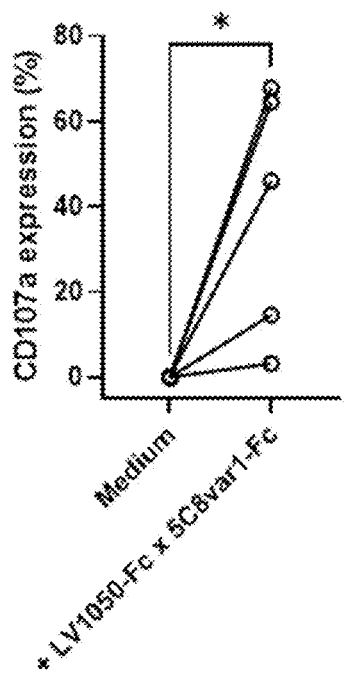
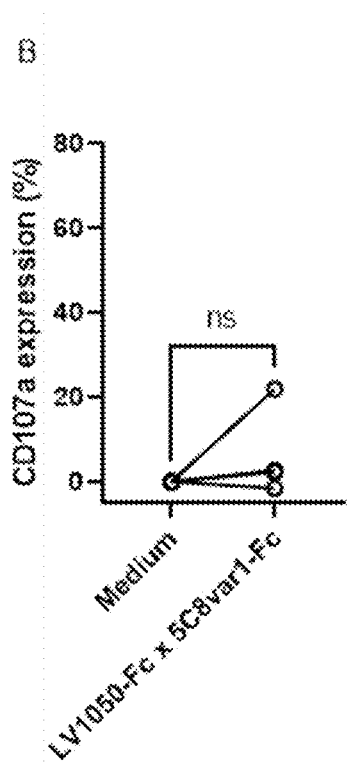

Fig. 16
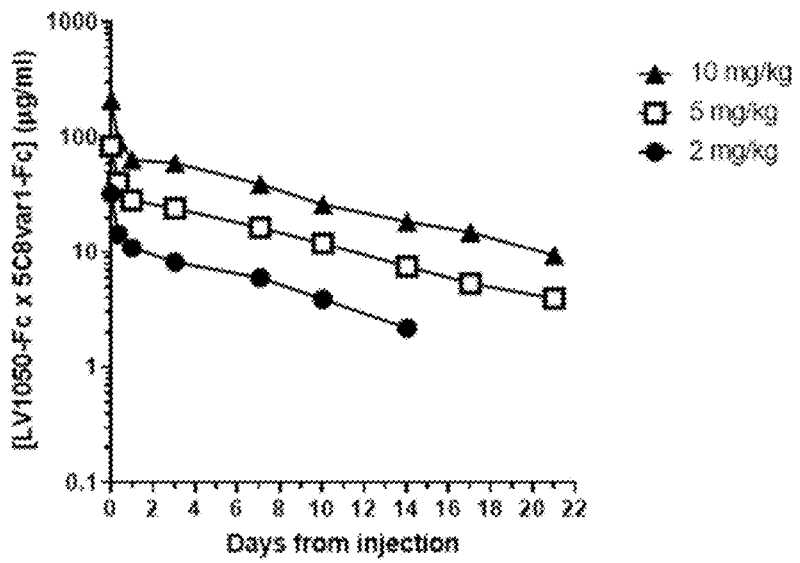
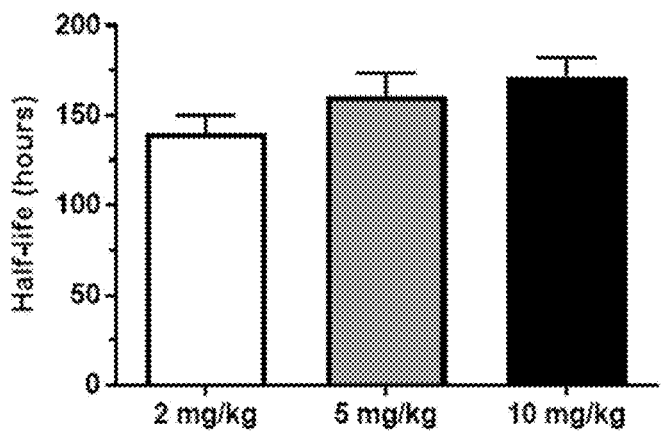
|  | Half-life (hours) |
|---|---|
| 2 mg/kg | 139.9±10.2 |
| 5 mg/kg | 160.2±13.4 |
| 10 mg/kg | 171.7±10.6 |

SEQUENCE LISTING

```
Sequence total quantity: 36
SEQ ID NO: 1           moltype = AA  length = 109
FEATURE                Location/Qualifiers
REGION                 1..109
                       note = Antibody sequence
source                 1..109
                       mol_type = protein
                       organism = synthetic construct
SEQUENCE: 1
EVQLVESGGG LVQPGGSLTL SCAASRFMIS EYSMHWVRQA PGKGLEWVST INPAGTTDYA   60
ESVKGRFTIS RDNAKNTLYL QMNSLKPEDT AVYYCDGYGY RGQGTQVSS              109

SEQ ID NO: 2           moltype = AA  length = 111
FEATURE                Location/Qualifiers
REGION                 1..111
                       note = Antibody sequence
```

```
                        -continued source                  1..111
                        mol_type = protein
                        organism = synthetic construct
SEQUENCE: 2
EVQLVESGGG LVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGQGTQVTVS S            111

SEQ ID NO: 3            moltype = AA  length = 111
FEATURE                 Location/Qualifiers
REGION                  1..111
                        note = Antibody sequence
source                  1..111
                        mol_type = protein
                        organism = synthetic construct
SEQUENCE: 3
EVQLVESGGG SVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGLGTQVTVS S            111

SEQ ID NO: 4            moltype = AA  length = 130
FEATURE                 Location/Qualifiers
REGION                  1..130
                        note = Antibody sequence
source                  1..130
                        mol_type = protein
                        organism = synthetic construct
SEQUENCE: 4
EVQLVESGGG LVQAGGSLRL SCAASGRPFS NYAMGWFRQA PGKEREFVAA ISWSGGSTSY    60
ADSVKGRFTI SRDNAKNTVY LQMNSPKPED TAIYYCAAQF SGADYGFGRL GIRGYEYDYW   120
GQGTQVTVSS                                                          130

SEQ ID NO: 5            moltype = AA  length = 130
FEATURE                 Location/Qualifiers
REGION                  1..130
                        note = Antibody sequence
source                  1..130
                        mol_type = protein
                        organism = synthetic construct
SEQUENCE: 5
EVQLLESGGG SVQPGGSLRL SCAASGRPFS NYAMSWFRQA PGKEREFVSA ISWSGGSTSY    60
ADSVKGRFTI SRDNSKNTLY LQMNSLRAED TAVYYCAAQF SGADYGFGRL GIRGYEYDYW   120
GQGTQVTVSS                                                          130

SEQ ID NO: 6            moltype = AA  length = 5
FEATURE                 Location/Qualifiers
REGION                  1..5
                        note = linker sequence
source                  1..5
                        mol_type = protein
                        organism = synthetic construct
SEQUENCE: 6
GGGGS                                                                 5

SEQ ID NO: 7            moltype = AA  length = 246
FEATURE                 Location/Qualifiers
REGION                  1..246
                        note = Antibody sequence
source                  1..246
                        mol_type = protein
                        organism = synthetic construct
SEQUENCE: 7
EVQLVESGGG LVQPGGSLTL SCAASRFMIS EYSMHWVRQA PGKGLEWVST INPAGTTDYA    60
ESVKGRFTIS RDNAKNTLYL QMNSLKPEDT AVYYCDGYGY RGQGTQVTVS SGGGGSEVQL   120
VESGGGLVQA GGSLRLSCAA SGRPFSNYAM GWFRQAPGKE REFVAAISWS GGSTSYADSV   180
KGRFTISRDN AKNTVYLQMN SPKPEDTAIY YCAAQFSGAD YGFGRLGIRG YEYDYWGQGT   240
QVTVSS                                                              246

SEQ ID NO: 8            moltype = AA  length = 253
FEATURE                 Location/Qualifiers
REGION                  1..253
                        note = Antibody sequence
source                  1..253
                        mol_type = protein
                        organism = synthetic construct
SEQUENCE: 8
EVQLVESGGG LVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGQGTQVTVS SGGGGSEVQL   120
LESGGGSVQP GGSLRLSCAA SGRPFSNYAM SWFRQAPGKE REFVSAISWS GGSTSYADSV   180
KGRFTISRDN SKNTLYLQMN SLRAEDTAVY YCAAQFSGAD YGFGRLGIRG YEYDYWGQGT   240
QVTVSSAAAE PEA                                                      253
```

```
SEQ ID NO: 9              moltype = AA  length = 253
FEATURE                   Location/Qualifiers
REGION                    1..253
                          note = Antibody sequence
source                    1..253
                          mol_type = protein
                          organism = synthetic construct
SEQUENCE: 9
EVQLVESGGG SVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGLGTQVTVS SGGGGSEVQL   120
LESGGGSVQP GGSLRLSCAA SGRPFSNYAM SWFRQAPGKE REFVSAISWS GGSTSYADSV   180
KGRFTISRDN SKNTLYLQMN SLRAEDTAVY YCAAQFSGAD YGFGRLGIRG YEYDYWGQGT   240
QVTVSSAAAE PEA                                                     253

SEQ ID NO: 10             moltype = AA  length = 14
FEATURE                   Location/Qualifiers
REGION                    1..14
                          note = Antibody sequence
source                    1..14
                          mol_type = protein
                          organism = synthetic construct
SEQUENCE: 10
AAASDKTHTC PPCP                                                     14

SEQ ID NO: 11             moltype = AA  length = 216
FEATURE                   Location/Qualifiers
REGION                    1..216
                          note = Antibody sequence
source                    1..216
                          mol_type = protein
                          organism = synthetic construct
SEQUENCE: 11
APELLGGPSV FLFPPKPKDT LMISRTPEVT CVVVDVSHED PEVKFNWYVD GVEVHNAKTK    60
PREEQYNSTY RVVSVLTVLH QDWLNGKEYK CKVSNKALPA PIEKTISKAK GQPREPQVYT   120
LPPSRDELTK NQVSLTCLVK GFYPSDIAVE WESNGQPENN YKTTPPVLDS DGSFFLYSKL   180
TVDKSRWQQG NVFSCSVMHE ALHNHYTQKS LSLSPG                             216

SEQ ID NO: 12             moltype = AA  length = 230
FEATURE                   Location/Qualifiers
REGION                    1..230
                          note = Antibody sequence
source                    1..230
                          mol_type = protein
                          organism = synthetic construct
SEQUENCE: 12
AAASDKTHTC PPCPAPEFEG GPSVFLFPPK PKDTLMISRT PEVTCVVVDV SHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRD ELTKNQVSLW CLVKGFYPSD IAVEWESNGQ PENNYKTTPP   180
VLDSDGSFFL YSKLTVDKSR WQQGNVFSCS VMHEALHNHY TQKSLSLSPG              230

SEQ ID NO: 13             moltype = AA  length = 230
FEATURE                   Location/Qualifiers
REGION                    1..230
                          note = Antibody sequence
source                    1..230
                          mol_type = protein
                          organism = synthetic construct
SEQUENCE: 13
AAASDKTHTC PPCPAPEFEG GPSVFLFPPK PKDTLMISRT PEVTCVVVDV SHEDPEVKFN    60
WYVDGVEVHN AKTKPREEQY NSTYRVVSVL TVLHQDWLNG KEYKCKVSNK ALPAPIEKTI   120
SKAKGQPREP QVYTLPPSRD ELTKNQVSLS CAVKGFYPSD IAVEWESNGQ PENNYKTTPP   180
VLDSDGSFFL VSKLTVDKSR WQQGNVFSCS VMHEALHNHY TQKSLSLSPG              230

SEQ ID NO: 14             moltype = AA  length = 10
FEATURE                   Location/Qualifiers
REGION                    1..10
                          note = Antibody sequence
source                    1..10
                          mol_type = protein
                          organism = synthetic construct
SEQUENCE: 14
RFMISEYSMH                                                          10

SEQ ID NO: 15             moltype = AA  length = 16
FEATURE                   Location/Qualifiers
REGION                    1..16
                          note = Antibody sequence
source                    1..16
```

```
                         mol_type = protein
                         organism = synthetic construct
SEQUENCE: 15
TINPAGTTDY ADSVKG                                                        16

SEQ ID NO: 16            moltype = AA   length = 5
FEATURE                  Location/Qualifiers
REGION                   1..5
                         note = Antibody sequence
source                   1..5
                         mol_type = protein
                         organism = synthetic construct
SEQUENCE: 16
DGYGY                                                                    5

SEQ ID NO: 17            moltype = AA   length = 5
FEATURE                  Location/Qualifiers
REGION                   1..5
                         note = Antibody sequence
source                   1..5
                         mol_type = protein
                         organism = synthetic construct
SEQUENCE: 17
NYAMS                                                                    5

SEQ ID NO: 18            moltype = AA   length = 17
FEATURE                  Location/Qualifiers
REGION                   1..17
                         note = Antibody sequence
source                   1..17
                         mol_type = protein
                         organism = synthetic construct
SEQUENCE: 18
AISWSGGSTS YADSVKG                                                       17

SEQ ID NO: 19            moltype = AA   length = 21
FEATURE                  Location/Qualifiers
REGION                   1..21
                         note = Antibody sequence
source                   1..21
                         mol_type = protein
                         organism = synthetic construct
SEQUENCE: 19
QFSGADYGFG RLGIRGYEYD Y                                                  21

SEQ ID NO: 20            moltype = AA   length = 126
FEATURE                  Location/Qualifiers
REGION                   1..126
                         note = Antibody sequence
source                   1..126
                         mol_type = protein
                         organism = synthetic construct
SEQUENCE: 20
EVQLVESGGG LVQAGGSLRL SCAASGRPFS NYGMGWFRQA PGKKREFVAG ISWSGGSTDY        60
ADSVKGRFTI SRDNAKNTVY LQMNSLKPED TAVYYCAAVF SGAETAYYPS DDYDYWGQGT        120
QVTVSS                                                                   126

SEQ ID NO: 21            moltype = AA   length = 10
FEATURE                  Location/Qualifiers
REGION                   1..10
                         note = Antibody sequence
source                   1..10
                         mol_type = protein
                         organism = synthetic construct
SEQUENCE: 21
GRPFSNYGMG                                                               10

SEQ ID NO: 22            moltype = AA   length = 17
FEATURE                  Location/Qualifiers
REGION                   1..17
                         note = Antibody sequence
source                   1..17
                         mol_type = protein
                         organism = synthetic construct
SEQUENCE: 22
GISWSGGSTD YADSVKG                                                       17

SEQ ID NO: 23            moltype = AA   length = 17
FEATURE                  Location/Qualifiers
```

```
REGION                         1..17
                               note = Antibody sequence
source                         1..17
                               mol_type = protein
                               organism = synthetic construct
SEQUENCE: 23
VFSGAETAYY PSDDYDY                                                          17

SEQ ID NO: 24                  moltype = AA  length = 750
FEATURE                        Location/Qualifiers
source                         1..750
                               mol_type = protein
                               organism = Homo sapiens
SEQUENCE: 24
MWNLLHETDS AVATARRPRW LCAGALVLAG GFFLLGFLFG WFIKSSNEAT NITPKHNMKA            60
FLDELKAENI KKFLYNFTQI PHLAGTEQNF QLAKQIQSQW KEFGLDSVEL AHYDVLLSYP           120
NKTHPNYISI INEDGNEIFN TSLFEPPPPG YENVSDIVPP FSAFSPQGMP EGDLVYVNYA           180
RTEDFFKLER DMKINCSGKI VIARYGKVFR GNKVKNAQLA GAKGVILYSD PADYFAPGVK           240
SYPDGWNLPG GGVQRGNILN LNGAGDPLTP GYPANEYAYR RGIAEAVGLP SIPVHPIGYY           300
DAQKLLEKMG GSAPPDSSWR GSLKVPYNVG PGFTGNFSTQ KVKMHIHSTN EVTRIYNVIG           360
TLRGAVEPDR YVILGGHRDS WVFGGIDPQS GAAVVHEIVR SFGTLKKEGW RPRRTILFAS           420
WDAEEFGLLG STEWAEENSR LLQERGVAYI NADSSIEGNY TLRVDCTPLM YSLVHNLTKE           480
LKSPDEGFEG KSLYESWTKK SPSPEFSGMP RISKLGSGND FEVFFQRLGI ASGRARYTKN           540
WETNKFSGYP LYHSVYETYE LVEKFYDPMF KYHLTVAQVR GGMVFELANS IVLPFDCRDY           600
AVVLRKYADK IYSISMKHPQ EMKTYSVSFD SLFSAVKNFT EIASKFSERL QDFDKSNPIV           660
LRMMNDQLMF LERAFIDPLG LPDRPFYRHV IYAPSSHNKY AGESFPGIYD ALFDIESKVD           720
PSKAWGEVKR QIYVAAFTVQ AAAETLSEVA                                           750

SEQ ID NO: 25                  moltype = AA  length = 360
FEATURE                        Location/Qualifiers
REGION                         1..360
                               note = Antibody sequence
source                         1..360
                               mol_type = protein
                               organism = synthetic construct
SEQUENCE: 25
EVQLLESGGG SVQPGGSLRL SCAASGRPFS NYAMSWFRQA PGKEREFVSA ISWSGGSTSY            60
ADSVKGRFTI SRDNSKNTLY LQMNSLRAED TAVYYCAAQF SGADYGFGRL GIRGYEYDYW           120
GQGTQVTVSS AAASDKTHTC PPCPAPEFEG GPSVFLFPPK PKDTLMISRT PEVTCVVVDV           180
SHEDPEVKFN WYVDGVEVHN AKTKPREEQY NSTYRVVSVL TVLHQDWLNG KEYKCKVSNK           240
ALPAPIEKTI SKAKGQPREP QVYTLPPSRD ELTKNQVSLW CLVKGFYPSD IAVEWESNGQ           300
PENNYKTTPP VLDSDGSFFL YSKLTVDKSR WQQGNVFSCS VMHEALHNHY TQKSLSLSPG           360

SEQ ID NO: 26                  moltype = AA  length = 341
FEATURE                        Location/Qualifiers
REGION                         1..341
                               note = Antibody sequence
source                         1..341
                               mol_type = protein
                               organism = synthetic construct
SEQUENCE: 26
EVQLVESGGG LVQPGGSLRL SCAASRFMIS EYSMHWVRQA PGKGLEWVST INPAGTTDYA            60
DSVKGRFTIS RDNAKNTLYL QMNSLRAEDT AVYYCDGYGY RGQGTQVTVS SAAASDKTHT           120
CPPCPAPEFE GGPSVFLFPP KPKDTLMISR TPEVTCVVVD VSHEDPEVKF NWYVDGVEVH           180
NAKTKPREEQ YNSTYRVVSV LTVLHQDWLN GKEYKCKVSN KALPAPIEKT ISKAKGQPRE           240
PQVYTLPPSR DELTKNQVSL SCAVKGFYPS DIAVEWESNG QPENNYKTTP PVLDSDGSFF           300
LVSKLTVDKS RWQQGNVFSC SVMHEALHNH YTQKSLSLSP G                              341

SEQ ID NO: 27                  moltype = AA  length = 361
FEATURE                        Location/Qualifiers
REGION                         1..361
                               note = Antibody sequence
source                         1..361
                               mol_type = protein
                               organism = synthetic construct
SEQUENCE: 27
EVQLLESGGG SVQPGGSLRL SCAASGRPFS NYAMSWFRQA PGKEREFVSA ISWSGGSTSY            60
ADSVKGRFTI SRDNSKNTLY LQMNSLRAED TAVYYCAAQF SGADYGFGRL GIRGYEYDYW           120
GQGTQVTVSS AAASDKTHTC PPCPAPEFEG GPSVFLFPPK PKDTLMISRT PEVTCVVVDV           180
SHEDPEVKFN WYVDGVEVHN AKTKPREEQY NSTYRVVSVL TVLHQDWLNG KEYKCKVSNK           240
ALPAPIEKTI SKAKGQPREP QVYTLPPSRD ELTKNQVSLW CLVKGFYPSD IAVEWESNGQ           300
PENNYKTTPP VLDSDGSFFL YSKLTVDKSR WQQGNVFSCS VMHEALHNHY TQKSLSLSPG           360
K                                                                          361

SEQ ID NO: 28                  moltype = AA  length = 342
FEATURE                        Location/Qualifiers
REGION                         1..342
                               note = Antibody sequence
source                         1..342
```

```
                            mol_type = protein
                            organism = synthetic construct
SEQUENCE: 28
EVQLVESGGG LVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGQGTQVTVS SAAASDKTHT   120
CPPCPAPEFE GGPSVFLFPP KPKDTLMISR TPEVTCVVVD VSHEDPEVKF NWYVDGVEVH   180
NAKTKPREEQ YNSTYRVVSV LTVLHQDWLN GKEYKCKVSN KALPAPIEKT ISKAKGQPRE   240
PQVYTLPPSR DELTKNQVSL SCAVKGFYPS DIAVEWESNG QPENNYKTTP PVLDSDGSFF   300
LVSKLTVDKS RWQQGNVFSC SVMHEALHNH YTQKSLSLSP GK                     342

SEQ ID NO: 29               moltype = AA  length = 246
FEATURE                     Location/Qualifiers
REGION                      1..246
                            note = antibody sequence
source                      1..246
                            mol_type = protein
                            organism = synthetic construct
SEQUENCE: 29
EVQLVESGGG LVQPGGSLRL SCAASRFMIS EYSMHWVRQA PGKGLEWVST INPAGTTDYA    60
DSVKGRFTIS RDNAKNTLYL QMNSLRAEDT AVYYCDGYGY RGQGTQVTVS SGGGGSEVQL   120
LESGGGSVQP GGSLRLSCAA SGRPFSNYAM SWFRQAPGKE REFVSAISWS GGSTSYADSV   180
KGRFTISRDN SKNTLYLQMN SLRAEDTAVY YCAAQFSGAD YGFGRLGIRG YEYDYWGQGT   240
QVTVSS                                                              246

SEQ ID NO: 30               moltype = AA  length = 737
FEATURE                     Location/Qualifiers
source                      1..737
                            mol_type = protein
                            organism = Homo sapiens
SEQUENCE: 30
MARPLCTLLL LMATLAGALA GSHHHHHHGS KSSNEATNIT PKHNMKAFLD ELKAENIKKF    60
LYNFTQIPHL AGTEQNFQLA KQIQSQWKEF GLDSVELAHY DVLLSYPNKT HPNYISIINE   120
DGNEIFNTSL FEPPPPGYEN VSDIVPPFSA FSPQGMPEGD LVYVNYARTE DFFKLERDMK   180
INCSGKIVIA RYGKVFRGNK VKNAQLAGAK GVILYSDPAD YFAPGVKSYP DGWNLPGGGV   240
QRGNILNLNG AGDPLTPGYP ANEYAYRRGI AEAVGLPSIP VHPIGYYDAQ KLLEKMGGSA   300
PPDSSWRGSL KVPYNVGPGF TGNFSTQKVK MHIHSTNEVT RIYNVIGTLR GAVEPDRYVI   360
LGGHRDSWVF GGIDPQSGAA VVHEIVRSFG TLKKEGWRPR RTILFASWDA EEFGLLGSTE   420
WAEENSRLLQ ERGVAYINAD SSIEGNYTLR VDCTPLMYSL VHNLTKELKS PDEGFEGKSL   480
YESWTKKSPS PEFSGMPRIS KLGSGNDFEV FFQRLGIASG RARYTKNWET NKFSGYPLYH   540
SVYETYELVE KFYDPMFKYH LTVAQVRGGM VFELANSIVL PFDCRDYAVV LRKYADKIYS   600
ISMKHPQEMK TYSVSFDSLF SAVKNFTEIA SKFSERLQDF DKSNPIVLRM MNDQLMFLER   660
AFIDPLGLPD RPFYRHVIYA PSSHNKYAGE SFPGIYDALF DIESKVDPSK AWGEVKRQIY   720
VAAFTVQAAA ETLSEVA                                                  737

SEQ ID NO: 31               moltype = AA  length = 503
FEATURE                     Location/Qualifiers
REGION                      1..503
                            note = gammadelta TCR construct
source                      1..503
                            mol_type = protein
                            organism = synthetic construct
SEQUENCE: 31
MQRISSLIHL SLFWAGVMSA IELVPEHQTV PVSIGVPATL RCSMKGEAIG NYYINWYRKT    60
QGNTMTFIYR EKDIYGPGFK DNFQGDIDIA KNLAVLKILA PSERDEGSYY CACDTLGMGG   120
EYTDKLIFGK GTRVTVEPRS QPHTKPSVFV MKNGTNVACL VKEFYPKDIR INLVSSKKIT   180
EFDPAIVISP SGKYNAVKLG KYEDSNSVTC SVQHDNKTVH STDFEVKTDS TDHVKPKETE   240
NTKQPSKSCH KPKAIVHTEK VNMMSLTAAA SDKTHTCPPC PAPELLGGPS VFLFPPKPKD   300
TLMISRTPEV TCVVVDVSHE DPEVKFNWYV DGVEVHNAKT KPREEQYNST YRVVSVLTVL   360
HQDWLNGKEY KCKVSNKALP APIEKTISKA KGQPREPQVY TLPPSRDELT KNQVSLSCAV   420
KGFYPSDIAV EWESNGQPEN NYKTTPPVLD SDGSFFLVSK LTVDKSRWQQ GNVFSCSVMH   480
EALHNHYTQK SLSLSPGHHH HHH                                           503

SEQ ID NO: 32               moltype = AA  length = 517
FEATURE                     Location/Qualifiers
REGION                      1..517
                            note = gammadelta TCR construct
source                      1..517
                            mol_type = protein
                            organism = synthetic construct
SEQUENCE: 32
MLSLLHASTL AVLGALCVYG AGHLEQPQIS STKTLSKTAR LECVVSGITI SATSVYWYRE    60
RPGEVIQFLV SISYDGTVRK ESGIPSGKFE VDRIPETSTS TLTIHNVEKQ DIATYYCALW   120
EAQQELGKKI KVFGPGTKLI ITDKQLDADV SPKPTIFLPS IAETKLQKAG TYLCLLEKFF   180
PDVIKIHWEE KKSNTILGSQ EGNTMKTNDT YMKFSWLTVP EKSLDKEHRC IVRHENNKNG   240
VDQEIIFPPI KTDVITMDPK DNCSKDANDT LLLQLTNTSA YAAASDKTHTC PPCPAPELLG   300
GPSVFLFPPK PKDTLMISRT PEVTCVVVDV SHEDPEVKFN WYVDGVEVHN AKTKPREEQY   360
NSTYRVVSVL TVLHQDWLNG KEYKCKVSNK ALPAPIEKTI SKAKGQPREP QVYTLPPSRD   420
ELTKNQVSLW CLVKGFYPSD IAVEWESNGQ PENNYKTTPP VLDSDGSFFL YSKLTVDKSR   480
WQQGNVFSCS VMHEALHNHY TQKSLSLSPG AAAEPEA                            517
```

```
SEQ ID NO: 33          moltype = AA   length = 31
FEATURE                Location/Qualifiers
source                 1..31
                       mol_type = protein
                       organism = Homo sapiens
SEQUENCE: 33
RTEDFFKLER DMKINCSGKI VIARYGKVFR G                                     31

SEQ ID NO: 34          moltype = AA   length = 21
FEATURE                Location/Qualifiers
source                 1..21
                       mol_type = protein
                       organism = Homo sapiens
SEQUENCE: 34
GSAPPDSSWR GSLKVPYNVG P                                                21

SEQ ID NO: 35          moltype = AA   length = 21
FEATURE                Location/Qualifiers
source                 1..21
                       mol_type = protein
                       organism = Homo sapiens
SEQUENCE: 35
IYSISMKHPQ EMKTYSVSFD S                                                21

SEQ ID NO: 36          moltype = AA   length = 21
FEATURE                Location/Qualifiers
source                 1..21
                       mol_type = protein
                       organism = Homo sapiens
SEQUENCE: 36
PSKAWGEVKR QIYVAAFTVQ A                                                21
```

ANTIBODIES THAT BIND PSMA AND GAMMA-DELTA T CELL RECEPTORS

CROSS-REFERENCE TO RELATED APPLICATIONS

This application is a continuation application of U.S. application Ser. No. 18/014,457, which is a US National Phase Application of PCT/EP2021/068960, filed on Jul. 8, 2021, which claims the benefit of priority to European Patent Application Number 20184800.9, filed Jul. 8, 2020, the entire contents of which are hereby incorporated by reference.

REFERENCE TO THE ELECTRONIC SEQUENCE FILE

The contents of the electronic sequence listing (LVAT_020_02US_SeqList_ST26.xml; Size: 48,600 bytes; and Date of Creation: Apr. 2, 2024) are herein incorporated by reference in its entirety.

FIELD OF THE INVENTION

The present invention relates to novel multispecific antibodies capable of binding human PSMA and capable of binding a human Vγ9Vδ2 T cell receptor. The invention further relates to pharmaceutical compositions comprising the antibodies of the invention and to uses of the antibodies of the invention for medical treatment.

BACKGROUND OF THE INVENTION

Prostate cancer is the most common cancer in men in Europe and the United States. Early detection of localized disease results in high survival rates. However, metastasized tumors lead to dramatically reduced survival. Prostate-specific membrane antigen (PSMA), also known as folate hydrolase I or glutamate carboxypeptidase II, is a potential target for drug development. PSMA is a type II transmembrane protein showing overexpression on prostatic cancer cells, but low expression in normal tissues.

Several PSMA-targeting molecules have been developed (see e.g. Haberkorn et a. (2016) Clin Cancer Res 22:9), including antibodies (Chatalic et al. (2015) J Nucl Med 56:1094; WO2018098354). Bispecific PSMA+CD3 T-cell engaging antibody approaches have also been described (Hernandez-Hoyos et al. (2016) Mol Cancer Ther 15:2155; WO2016187594). Bispecific T-cell engaging antibodies have a tumor target binding specificity and a T-cell binding specificity and thus boost efficacy by re-directing T-cell cytotoxicity to malignant cells, see e.g. Huehls et al. (2015) Immunol Cell Biol 93:290; Ellerman (2019) Methods, 154:102; de Bruin et al. (2017) Oncoimmunology 7(1):e1375641 and WO2015156673. However, results vary significantly. For example, in one study in which a CD3 binding moiety was combined with binding moieties against 8 different B-cell targets (CD20, CD22, CD24, CD37, CD70, CD79b, CD138 and HLA-DR), it was found that the bispecific antibodies targeting the different tumor targets showed strong variation in their capacity to induce target cell cytotoxicity and that cytotoxicity did not correlate with antigen expression levels. For example, CD3-based bispecific antibodies targeting HLA-DR or CD138 were not able to induce cytotoxicity in spite of intermediate to high HLA-DR and CD138 expression levels (Engelberts et al. (2020) Ebiomedicine 52:102625). Few T-cell redirecting therapies have reached late-stage clinical development, possibly due to significant toxicity, manufacturing problems, immunogenicity, and low response rates in solid tumors. In particular, toxicity may occur when the T-cell engager includes a CD3 binding arm as a result of uncontrolled immune activation and cytokine release.

Thus, while significant progress has been made, there is still a need for novel PSMA antibodies that are therapeutically effective yet have acceptable toxicity. Such novel PSMA antibodies should also have appropriate pharmacokinetic and pharmacodynamic properties and optimally be manufacturable with high yield and purity. Furthermore, stable formations of such antibodies are needed in which minimal degradation and aggregation occurs.

These needs are addressed by the present invention.

SUMMARY OF THE INVENTION

The present invention provides novel antibodies for PSMA-based therapy. Bispecific antibodies were constructed in which PSMA-binding regions were combined with binding regions capable of binding a Vγ9Vδ2 T cell receptor and thus engaging T cells. Surprisingly, the bispecific antibodies were able to mediate activation of autologous Vγ9Vδ2 T cells, including tumor-infiltrating Vγ9Vδ2 T cells, and to induce killing of patient-derived tumor cells in the presence of autologous PBMC-derived Vγ9Vδ2 T cells with very high potency. These activities were also observed using tumor cell lines at low effector cell (γδ T cell) to target cell (tumor cell) ratios, which is important, because γδ T cells are only a subpopulation of T cells in humans which can vary in numbers. Normal healthy tissue, on the other hand, was not affected, indicating the potential of these antibodies for an efficacious yet safe cancer treatment. In addition, studies with whole human blood indicate that in spite of the high potency on target cells, the antibody only induced low levels of cytokine release, suggesting a low risk of cytokine release syndrome.

Furthermore, a novel bispecific VHH-human-Fc-containing antibody format was developed which, when produced in mammalian host cells, yielded a highly homogenous and pure product. Moreover, the format had suitable pharmacokinetic properties for use in medical treatment and a suitable stable formulation for this product was developed. Without being bound by any specific theory, the molecular size and decreased hydrodynamic radius of the format may be highly suitable for tumor penetration, yet avoid renal filtration and ensure, via binding to FcRn, protection from degradation.

Accordingly, in a first aspect, the invention provides a multispecific antibody comprising a first antigen-binding region capable of binding human PSMA and a second antigen-binding region capable of binding a human Vγ9Vδ2 T cell receptor.

In further aspects, the invention relates to pharmaceutical compositions comprising the antibodies of the invention, uses of the antibodies of the invention in medical treatment, and to nucleic acid constructs, expression vectors for producing antibodies of the invention and to host cells comprising such nucleic acid constructs or expression vector.

Further aspects and embodiments of the invention are described below.

BRIEF DESCRIPTION OF THE DRAWINGS

FIG. 1: Sequence alignment of humanization variants of the anti-PSMA VHH JVZ-007. LV1044 is the original llama-derived sequence; the other sequences are humanized variants.

FIG. 3: T cell activation assay (degranulation) testing the potency of humanization variants in inducing T cell degranulation. Upper panel: Titration of bispecific constructs using PSMA-positive LNCaP cells as target cells. Lower panel: a single high (10 nM) concentration of bispecific constructs used in a degranulation assay using PC-3 cells as target cells. 5C8 indicates the anti-Vγ9Vδ2 TCR-specific VHH and 5C8var1 is the humanized variant thereof.

FIG. 5: Binding of LV1050-Fc×5C8var1-Fc to different cells/cell lines in FACS. Upper panel: Binding to PSMA-positive cell line LNCaP and to the PSMA-negative line PC-3. Lower panel: binding to Vγ9Vδ2T cells.

FIG. 6: Target dependent, LV1050-Fc×5C8var1-Fc-induced Vγ9Vδ2 T cell activation (upper panel) and cytotoxicity (lower panel).

FIG. 7: Expression levels of PSMA and CD277 on tumor tissue and normal prostate tissue and frequency (as part of the total CD3+ population) of Vγ9Vδ2-T cells in the tissues.

FIG. 8: Cytotoxicity (24-hour assay) of prostate tumor cells induced by Vγ9Vδ2T cells and LV1044-5C8 ("LAVA compound"). *** $p<0.05$. The number of tumor cells (upper panel) or normal cells (lower panel) without treatment was put at 100%.

FIG. 12: Degranulation of Vγ9Vδ2-T cells endogenously present in prostate tumor or normal (non-malignant) tissue. Prostate tumor (A) and normal (non-malignant) prostate tissue (B) cell suspensions were incubated for 4 hours with a fluorescently labeled CD107a mAb with or without 50 nM of LV1050-Fc×5C8var1-Fc, and the percentage of CD45+/CD3+/Vγ9+/Vδ2+/CD107a+ cells (indicated as CD107a expression (% of EpCAM–/CD45+/CD3+/Vγ9+/Vδ2+)) was determined by flow cytometry. The induction of CD107a expression by LV1050-Fc×5C8var1-Fc was expressed relative to the background (medium only) expression. **$P<0.01$, paired T-test; ns=not significant.

FIG. 13: Degranulation of Vγ9Vδ2-T cells present in autologous PMBC upon co-culture with patient-derived prostate tumor or normal (non-malignant) prostate tissue. Prostate tumor (A) and normal (non-malignant) prostate tissue (B) cell suspensions were incubated for 4 hours with a fluorescently labeled CD107a mAb with or without 50 nM of LV1050-Fc×5C8var1-Fc in the presence of autologous PBMC, and the percentage of CD45+/CD3+/Vγ9+/Vδ2+/CD107a+ cells (indicated as CD107a expression (% of EpCAM–/CD45+/CD3+/Vγ9+/Vδ2+) was determined by flow cytometry. The induction of CD107a expression by LV1050-Fc×5C8var1-Fc was expressed relative to the background (medium only) expression. *$P<0.05$, paired-T test; ns=not significant.

FIG. 16: Pharmacokinetics of LV1050-Fc×5C8var1-Fc in human FcRn transgenic mice after a single IV dose. LV1050-Fc×5C8var1-Fc and a humanized IgG control antibody were co-administered intravenously at 2 mg/kg, 5 mg/kg or 10 mg/kg per group in human FcRn transgenic mice (n=4 per group). The upper graph shows the concentration of LV1050-Fc×5C8var1-Fc over time for the three groups of mice dosed with different concentrations of the antibody. The bottom graph shows LV1050-Fc×5C8var1-Fc terminal half-life calculations obtained in the three dosage groups (using PK Solutions software to analyze the ELISA data). LV1050-Fc×5C8var1-Fc half-lives calculated for each group co-administered with IgG control antibody were comparable and corresponded to 139.9±10.2 hours (at 2 mg/kg), 160.2±13.4 hours (at 5 mg/kg) and 171.7±10.6 hours (at 10 mg/kg).

DETAILED DESCRIPTION OF THE INVENTION

Definitions

Figure 2:
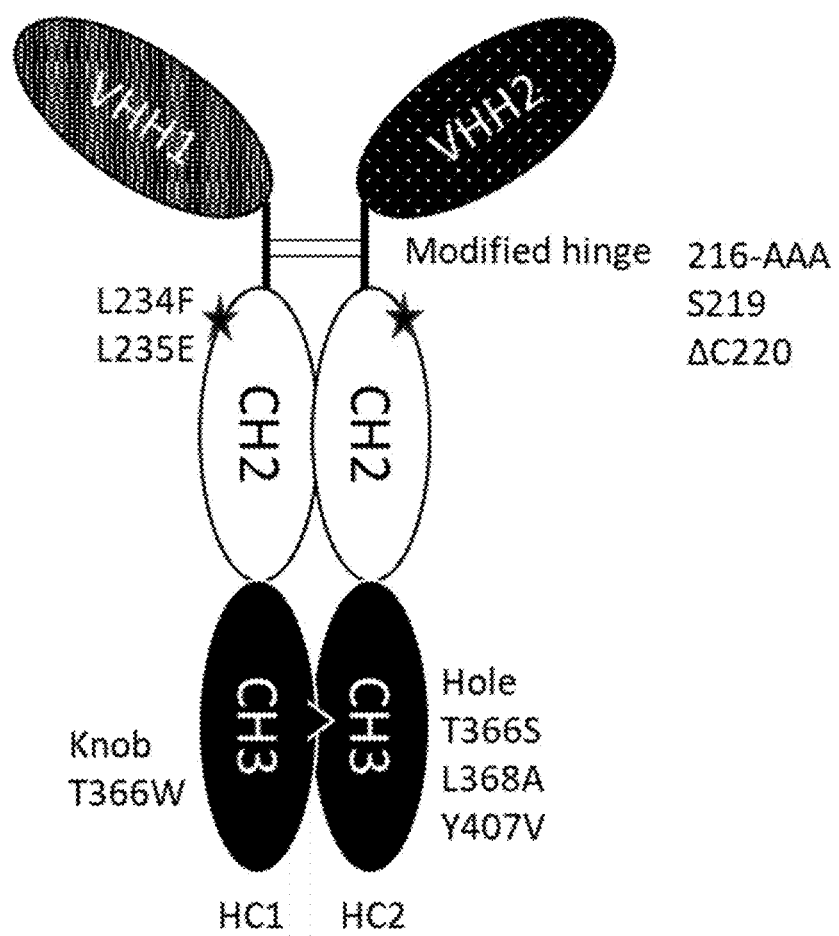
FIG. 2: Schematic representation of the half-life extended format of the bispecific VHHs. Fc silencing mutations are indicated by the asterisks. The sequence of the modified hinge is indicated next to the figure, as well as the CH3 mutations that confer the KiH mediated hetero-dimerization. HC: heavy chain.

The term "human PSMA", when used herein, refers to the human Prostate-Specific Membrane Antigen protein, also known as glutamate carboxypeptidase 2 (EC:3.4.17.21), cell growth-inhibiting gene 27 protein, Folate hydrolase 1, Folylpoly-gamma-glutamate carboxypeptidase (FGCP), glutamate carboxypeptidase II (GCPII), membrane glutamate carboxypeptidase (mGCP), N-acetylated-alpha-linked acidic dipeptidase I (NAALADase I) or pteroylpoly-gamma-glutamate carboxypeptidase (UniProtKB-Q04609 (FOLH1_HUMAN)), Isoform I, set forth in SEQ ID NO:24.

The term "human Vδ2", when used herein, refers to the TRDV2 protein, T cell receptor delta variable 2 (UniProtKB—A0JD36 (A0JD36_HUMAN) gives an example of a Vδ2 sequence).

The term "human Vγ9", when used herein, refers to the TRGV9 protein, T cell receptor gamma variable 9 (UniProtKB—Q99603_HUMAN gives an example of a Vγ9 sequence).

The term "antibody" is intended to refer to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The antigen-binding region (or antigen-binding domain) which interacts with an antigen may comprise variable regions of both the heavy and light chains of the immunoglobulin molecule or may be a single-domain antigen-binding region, e.g. a heavy chain variable region only. The constant regions of an antibody, if present, may mediate the binding of the immunoglobulin to host tissues or factors, including various cells of the immune system (such as effector cells and T cells) and components of the complement system such as C1q, the first component in the classical pathway of complement activation. In some embodiments, however, the Fc region of the antibody has been modified to become inert, "inert" means an Fc region which is at least not able to bind any Fcγ Receptors, induce Fc-mediated cross-linking of FcRs, or induce FcR-mediated cross-linking of target antigens via two Fc regions of individual antibodies. In a further embodiment, the inert Fc region is in addition not able to bind C1q. In one embodiment, the antibody contains mutations at positions 234 and 235 (Canfield and Morrison (1991) J Exp Med 173:1483), e.g. a Leu to Phe mutation at position 234 and a Leu to Glu mutation at position 235. In another embodiment, the antibody contains a Leu to Ala mutation at position 234, a Leu to Ala mutation at position 235 and a Pro to Gly mutation at position 329. In another embodiment, the antibody contains a Leu to Phe mutation at position 234, a Leu to Glu mutation at position 235 and an Asp to Ala at position 265.

The Fc region of an immunoglobulin is defined as the fragment of an antibody which would be typically generated after digestion of an antibody with papain which includes the two CH2-CH3 regions of an immunoglobulin and a connecting region, e.g. a hinge region. The constant domain of an antibody heavy chain defines the antibody isotype, e.g. IgG1, IgG2, IgG3, IgG4, IgA1, IgA2, IgM, IgD, or IgE. The Fc-region mediates the effector functions of antibodies with cell surface receptors called Fc receptors and proteins of the complement system.

The term "hinge region" as used herein is intended to refer to the hinge region of an immunoglobulin heavy chain. Thus, for example the hinge region of a human IgG1 antibody corresponds to amino acids 216-230 according to the EU numbering.

The term "CH2 region" or "CH2 domain" as used herein is intended to refer to the CH2 region of an immunoglobulin heavy chain. Thus, for example the CH2 region of a human IgG1 antibody corresponds to amino acids 231-340 according to the EU numbering. However, the CH2 region may also be any of the other subtypes as described herein.

The term "CH3 region" or "CH3 domain" as used herein is intended to refer to the CH3 region of an immunoglobulin heavy chain. Thus, for example the CH3 region of a human IgG1 antibody corresponds to amino acids 341-447 according to the EU numbering. However, the CH3 region may also be any of the other subtypes as described herein.

Reference to amino acid positions in the Fc region/Fc domain in the present invention is according to the EU-numbering (Edelman et al., Proc Natl Acad Sci USA. 1969 May;63(1):78-85; Kabat et al., Sequences of proteins of immunological interest. 5th Edition—1991 NIH Publication No. 91-3242).

As indicated above, the term antibody as used herein, unless otherwise stated or clearly contradicted by context, includes fragments of an antibody that retain the ability to specifically bind to the antigen. It has been shown that the antigen-binding function of an antibody may be performed by fragments of a full-length antibody. Examples of binding fragments encompassed within the term "antibody" include (i) a Fab' or Fab fragment, i.e. a monovalent fragment consisting of the VL, VH, CL and CH1 domains, or a monovalent antibody as described in WO2007059782; (ii) F(ab')2 fragments, i.e. bivalent fragments comprising two Fab fragments linked by a disulfide bridge at the hinge region; (iii) a Fd fragment consisting essentially of the VH and CH1 domains; and (iv) a Fv fragment consisting essentially of the VL and VH domains of a single arm of an antibody. Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise indicated by context. Although such fragments are generally included within the meaning of antibody, they collectively and each independently are unique features of the present invention, exhibiting different biological properties and utility. The term antibody, unless specified otherwise, also includes polyclonal antibodies, monoclonal antibodies (mAbs), chimeric antibodies and humanized antibodies, and antibody fragments provided by any known technique, such as enzymatic cleavage, peptide synthesis, and recombinant techniques.

In some embodiments of the antibodies of the invention, the first antigen-binding region or the antigen-binding region, or both, is a single domain antibody. Single domain antibodies (sdAb, also called Nanobody®, or VHH) are well known to the skilled person, see e.g. Hamers-Casterman et al. (1993) Nature 363:446, Roovers et al. (2007) Curr Opin Mol Ther 9:327 and Krah et al. (2016) Immunopharmacol Immunotoxicol 38:21. Single domain antibodies comprise a single CDR1, a single CDR2 and a single CDR3. Examples of single domain antibodies are variable fragments of heavy-chain-only antibodies, antibodies that naturally do not comprise light chains, single domain antibodies derived from conventional antibodies, and engineered antibodies. Single domain antibodies may be derived from any species including mouse, human, camel, llama, shark, goat, rabbit, and cow. For example, naturally occurring VHH molecules can be derived from antibodies raised in Camelidae species, for example in camel, dromedary, llama, alpaca and guanaco. Like a whole antibody, a single domain antibody is able to bind selectively to a specific antigen. Single domain antibodies may contain only the variable domain of an immunoglobulin chain, i.e. CDR1, CDR2 and CDR3 and framework regions.

The term "immunoglobulin" as used herein is intended to refer to a class of structurally related glycoproteins consisting of two pairs of polypeptide chains, one pair of light (L) chains and one pair of heavy (H) chains, all four potentially inter-connected by disulfide bonds. The term "immunoglobulin heavy chain", "heavy chain of an immunoglobulin" or "heavy chain" as used herein is intended to refer to one of the chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The heavy chain constant region further comprises a hinge region. Within the structure of the immunoglobulin (e.g. IgG), the two heavy chains are inter-connected via disulfide bonds in the hinge region. Equally to the heavy chains, each light chain is typically comprised of several regions; a light chain variable region (VL) and a light chain constant region (CL). Furthermore, the VH and VL regions may be subdivided into regions of hypervariability (or hypervariable regions which may be hypervariable in sequence and/or form structurally defined loops), also termed complementarity determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences may be determined by use of various methods, e.g. the methods provided by Choitia and Lesk (1987) J. Mol. Biol. 196:901 or Kabat et al. (1991) Sequence of protein of immunological interest, fifth edition. NIH publication. Various methods for CDR determination and amino acid numbering can be compared on www.abysis.org (UCL).

The term "isotype" as used herein, refers to the immunoglobulin (sub) class (for instance IgG1, IgG2, IgG3, IgG4, IgD, IgA, IgE, or IgM) or any allotype thereof, such as IgG1m(za) and IgG1m(f) that is encoded by heavy chain constant region genes. Each heavy chain isotype can be combined with either a kappa (κ) or lambda (λ) light chain. An antibody of the invention can possess any isotype.

The term "parent antibody", is to be understood as an antibody which is identical to an antibody according to the invention, but wherein the parent antibody does not have one or more of the specified mutations. A "variant" or "antibody variant" or a "variant of a parent antibody" of the present invention is an antibody molecule which comprises one or more mutations as compared to a "parent antibody". Amino acid substitutions may exchange a native amino acid for another naturally occurring amino acid, or for a non-naturally occurring amino acid derivative. The amino acid substitution may be conservative or non-conservative. In the context of the present invention, conservative substitutions may be defined by substitutions within the classes of amino acids reflected in one or more of the following three tables:

Amino Acid Residue Classes For Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues

| | |
|---|---|
| Alcohol group-containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, N, D, E, and R |

In the context of the present invention, a substitution in a variant is indicated as: Original amino acid—position—substituted amino acid; The three-letter code, or one letter code, are used, including the codes Xaa and X to indicate amino acid residue. Accordingly, the notation "T366W" means that the variant comprises a substitution of threonine with tryptophan in the variant amino acid position corresponding to the amino acid in position 366 in the parent antibody.

Furthermore, the term "a substitution" embraces a substitution into any one of the other nineteen natural amino acids, or into other amino acids, such as non-natural amino acids. For example, a substitution of amino acid T in position 366 includes each of the following substitutions:

366A, 366C, 366D, 366G, 366H, 366F, 366I, 366K, 366L, 366M, 366N, 366P, 366Q, 366R, 366S, 366E, 366V, 366W, and 366Y.

The term "full-length antibody" when used herein, refers to an antibody which contains all heavy and light chain constant and variable domains corresponding to those that are normally found in a wild-type antibody of that isotype.

The term "chimeric antibody" refers to an antibody wherein the variable region is derived from a non-human species (e.g. derived from rodents) and the constant region is derived from a different species, such as human. Chimeric antibodies may be generated by genetic engineering. Chimeric monoclonal antibodies for therapeutic applications are developed to reduce antibody immunogenicity.

The term "humanized antibody" refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and, optionally, fully human constant regions. Optionally, additional amino acid modifications, which are not necessarily back-mutations, may be introduced to obtain a humanized antibody with preferred characteristics, such as affinity and biochemical properties. Humanization of non-human therapeutic antibodies is performed to minimize its immunogenicity in man while such humanized antibodies at the same time maintain the specificity and binding affinity of the antibody of non-human origin.

The term "multispecific antibody" refers to an antibody having specificities for at least two different, such as at least three, typically non-overlapping, epitopes. Such epitopes may be on the same or on different target antigens. If the epitopes are on different targets, such targets may be on the same cell or different cells or cell types.

The term "bispecific antibody" refers to an antibody having specificities for two different, typically non-overlapping, epitopes. Such epitopes may be on the same or different targets. If the epitopes are on different targets, such targets may be on the same cell or different cells or cell types.

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) ScFv- and diabody-based and heavy chain antibodies (e.g., domain antibodies, Nanobodies®) wherein different single chain Fv molecules or different diabodies or different heavy-chain antibodies (e.g. domain antibodies, Nanobodies®) are fused to each other or to another protein or carrier molecule fused to heavy-chain constant-domains, Fc-regions or parts thereof.

Examples of IgG-like molecules with complementary CH3 domains molecules include but are not limited to the Triomab® (Trion Pharma/Fresenius Biotech), the Knobs-into-Holes (Genentech), CrossMAbs (Roche) and the electrostatically-matched (Amgen, Chugai, Oncomed), the LUZ-Y (Genentech, Wranik et al. J. Biol. Chem. 2012, 287(52): 43331-9, doi: 10.1074/jbc.M112.397869. Epub 2012 Nov. 1), DIG-body and PIG-body (Pharmabcine, WO2010134666, WO2014081202), the Strand Exchange Engineered Domain body (SEEDbody)(EMD Serono), the Biclonics (Merus, WO2013157953), FcΔAdp (Regeneron), bispecific IgG1 and IgG2 (Pfizer/Rinat), Azymetric scaffold (Zymeworks/Merck,), mAb-Fv (Xencor), bivalent bispecific antibodies (Roche, WO2009080254) and DuoBody® molecules (Genmab).

Examples of recombinant IgG-like dual targeting molecules include but are not limited to Dual Targeting (DT)-Ig (GSK/Domantis, WO2009058383), Two-in-one Antibody (Genentech, Bostrom, et al 2009. Science 323, 1610-1614), Cross-linked Mabs (Karmanos Cancer Center), mAb2 (F-Star), Zybodies™ (Zyngenia, LaFleur et al. MAbs. 2013 March-April;5(2):208-18), approaches with common light chain, κλBodies (NovImmune, WO2012023053) and CovX-body® (CovX/Pfizer, Doppalapudi, V. R., et al 2007. Bioorg. Med. Chem. Lett. 17,501-506).

Examples of IgG fusion molecules include but are not limited to Dual Variable Domain (DVD)-Ig (Abbott), Dual domain double head antibodies (Unilever; Sanofi Aventis), IgG-like Bispecific (ImClone/Eli Lilly, Lewis et al. Nat Biotechnol. 2014 February;32(2):191-8), Ts2Ab (MedImmune/AZ, Dimasi et al. J Mol Biol. 2009 October 30;393 (3):672-92) and BsAb (Zymogenetics, WO2010111625), HERCULES (Biogen Idec), scFv fusion (Novartis), scFv fusion (Changzhou Adam Biotech Inc) and TvAb (Roche).

Examples of Fc fusion molecules include but are not limited to ScFv/Fc Fusions (Academic Institution, Pearce et al Biochem Mol Biol Int. 1997 September;42(6):1179), SCORPION (Emergent BioSolutions/Trubion, Blankenship J W, et al. AACR 100th Annual meeting 2009 (Abstract #5465); Zymogenetics/BMS, WO2010111625), Dual Affinity Retargeting Technology (Fc-DART™) (MacroGenics) and Dual (ScFv)2-Fab (National Research Center for Antibody Medicine—China).

Examples of Fab fusion bispecific antibodies include but are not limited to F(ab)2 (Medarex/AMGEN), Dual-Action or Bis-Fab (Genentech), Dock-and-Lock® (DNL) (ImmunoMedics), Bivalent Bispecific (Biotecnol) and Fab-Fv (UCB-Celltech).

Examples of ScFv-, diabody-based and domain antibodies include but are not limited to Bispecific T Cell Engager (BiTE®) (Micromet, Tandem Diabody (Tandab) (Affimed), Dual Affinity Retargeting Technology (DART™) (MacroGenics), Single-chain Diabody (Academic, Lawrence FEBS Lett. 1998 April 3;425(3):479-84), TCR-like Antibodies (AIT, ReceptorLogics), Human Serum Albumin ScFv Fusion (Merrimack, WO2010059315) and COMBODY molecules (Epigen Biotech, Zhu et al. Immunol Cell Biol. 2010 August;88(6):667-75), dual targeting nanobodies® (Ablynx, Hmila et al., FASEB J. 2010), dual targeting heavy chain only domain antibodies.

In the context of antibody binding to an antigen, the terms "binds" or "specifically binds" refer to the binding of an antibody to a predetermined antigen or target (e.g. human PSMA or V 2) to which binding typically is with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less, e.g. when determined using flow cytometry as described in the Examples herein. Alternatively, apparent $K_D$ values can be determined using for instance surface plasmon resonance (SPR) technology in a BIAcore T200 instrument using the antigen as the ligand and the binding moiety or binding molecule as the analyte. Specific binding means that the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen. The degree with which the affinity is lower is dependent on the $K_D$ of the binding moiety or binding molecule, so that when the $K_D$ of the binding moiety or binding molecule is very low (that is, the binding moiety or binding molecule is highly specific), then the degree with which the affinity for the antigen is lower than the affinity for a non-specific antigen may be at least 10,000-fold. The term "$K_D$" (M), as used herein, refers to the dissociation equilibrium constant of a particular interaction between the antigen and the binding moiety or binding molecule.

In the context of the present invention, "competition" or "able to compete" or "competes" refers to any detectably significant reduction in the propensity for a particular binding molecule (e.g. a PSMA antibody) to bind a particular binding partner (e.g. PSMA) in the presence of another molecule (e.g. a different PSMA antibody) that binds the binding partner. Typically, competition means an at least about 25 percent reduction, such as an at least about 50 percent, e.g. an at least about 75 percent, such as an at least 90 percent reduction in binding, caused by the presence of another molecule, such as an antibody, as determined by, e.g., ELISA analysis or flow cytometry using sufficient amounts of the two or more competing molecules, e.g. antibodies. Additional methods for determining binding specificity by competitive inhibition may be found in for instance Harlow et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc, and Wiley Inter-Science N. Y., (1992, 1993), and Muller, Meth. Enzymol. 92, 589-601 (1983)). In one embodiment, the antibody of the present invention binds to the same epitope on PSMA as antibody LV1050 and/or to the same epitope on Vδ2 as antibody 5C8 or 6H4. Methods for determining the epitope of a binding molecule, such as an antibody, are known in the art.

The terms "first" and "second" antigen-binding regions when used herein do not refer to their orientation/position in the antibody, i.e. they have no meaning with regard to the N- or C-terminus. The terms "first" and "second" only serve to correctly and consistently refer to the two different antigen-binding regions in the claims and the description.

"Capable of binding a Vγ9Vδ2-TCR" means that the binding molecule can bind a Vγ9Vδ2-TCR, but does not exclude that the binding molecule binds to one of the separate subunits in the absence of the other subunit, i.e. to the Vγ9 chain alone or to the Vδ2 chain alone. For example, antibody 5C8 is an antibody that binds the Vγ9Vδ2-TCR, but also binds the Vδ2 chain when the Vδ2 chain is expressed alone. The term does also not exclude that the antibody is specific for the combination of the two chains.

"% sequence identity", when used herein, refers to the number of identical nucleotide or amino acid positions shared by different sequences (i.e., % identity=#of identical positions/total #of positions×100), taking into account the number of gaps, and the length of each gap, which need to be introduced for optimal alignment. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4.

Further Aspects and Embodiments of the Invention

As described above, in a first main aspect, the invention relates to a multispecific antibody comprising a first antigen-binding region capable of binding human PSMA and a second antigen-binding region capable of binding a human Vγ9Vδ2 T cell receptor.

In one embodiment, the multispecific antibody is a bispecific antibody. In another embodiment, the first antigen-binding region is a single-domain antibody. In another embodiment, the second antigen-binding region is a single-domain antibody. In a further embodiment, both the first antigen-antigen binding region and the second antigen-binding region are single-domain antibodies. In a further embodiment, the multispecific antibody is a bispecific antibody, wherein the first antigen-binding region is a single-domain antibody and the second antigen-binding region is a single-domain antibody.

In one embodiment, the multispecific antibody competes (i.e. is able to compete) for binding to human PSMA with an antibody having the sequence set forth in SEQ ID NO:2, preferably the multispecific antibody binds the same epitope on human PSMA as an antibody having the sequence set forth in SEQ ID NO:2. In one embodiment, the multispecific antibody binds to an epitope on human PSMA which comprises one or more, or all, of the following amino acid residues: R190, S197, R204, S317, R320, S322, K324, H618, S631, K729, R730 and Y733, wherein numbering is according to UniProt sequence Q04609-1. In a further embodiment, the first antigen-binding region comprises the VH CDR1 sequence set forth in SEQ ID NO:14, the VH CDR2 sequence set forth in SEQ ID NO:15 and the VH CDR3 sequence set forth in SEQ ID NO:16.

In a further embodiment, the first antigen-binding region is humanized, wherein preferably the first antigen-binding region comprises or consists of:
  (a) the sequence set forth in SEQ ID NO:2, or
  (b) a sequence having at least 90%, such as least 92%, e.g. at least 94%, such as at least 96%, e.g. at least 98% sequence identity to the sequence set forth in SEQ ID NO:2.

As described above, the multispecific antibody of the invention comprises a second antigen-binding region capable of binding a human Vγ9Vδ2-T cell receptor. In one embodiment, the multispecific antibody is able to activate human Vγ9Vδ2 T cells. The activation of the Vγ9Vδ2 T cells may be measured through gene-expression and/or (surface) marker expression (e.g., activation markers, such as CD25, CD69, or CD107a) and/or secretory protein (e.g., cytokines or chemokines) profiles. In a preferred embodiment, the multispecific antibody is able to induce activation (e.g. upregulation of CD69 and/or CD25 expression) resulting in degranulation marked by an increase in CD107a expression (see e.g. Example 5) and/or cytokine production (e.g. TNFα, IFNγ) by Vγ9Vδ2 T cells. Preferably, a multispecific antibody of the present invention is able to increase the number of cells positive for CD107a at least 2-fold, such as at least 5-fold, when tested as described in Example 5 herein. In another preferred embodiment, the multispecific antibody of the invention has an EC50 value for increasing the percentage of CD107a positive cells of 50 pM or less, such as 25 PM or less, e.g. 20 pM or less, such as 15 pM or less, e.g. 10 pM or less, or even 5 PM or less, such as 2 pM or less or 1 pM or less when tested using Vγ9Vδ2 T cells and LNCaP target cells as described herein in Example 5.

In one embodiment of the multispecific antibody of the invention, the multispecific antibody is capable of binding to human Vδ2. Vδ2 is part of the delta chain of the Vγ9Vδ2-TCR. An antibody capable of binding to human Vδ2 may bind an epitope that is entirely located within the V 2 region or bind an epitope that is a combination of residues in Vδ2 region and the constant region of the delta chain. In another embodiment, the multispecific antibody is capable of binding to human Vγ9. Vγ9 is part of the gamma chain of Vγ9Vδ2-TCR. An antibody capable of binding to human Vγ9 may bind an epitope that is entirely located within the Vγ9 region or bind an epitope that is a combination of residues in Vγ9 region and the constant region of the gamma chain. Several such antibodies which bind to Vδ2 or Vγ9 have been described in WO2015156673 and their antigen-binding regions at least the CDR sequences thereof can be incorporated in the multispecific antibody of the invention. Other examples of antibodies from which a Vγ9Vδ2-TCR-binding region might be derived are TCR Vγ9 antibody 7A5 (ThermoFisher) (Oberg et al. (2014) Cancer Res 74:1349) and antibodies B1.1 (ThermoFisher) and 5A6.E9 (ATCC HB 9772), both described in Neuman et al. (2016) J Med Prim 45:139.

In one embodiment, the multispecific antibody competes for binding to human Vδ2 with an antibody having the sequence set forth in SEQ ID NO:5 or competes for binding to human Vδ2 with an antibody having the sequence set forth in SEQ ID NO:20. In a further embodiment, the multispecific antibody binds the same epitope on human Vδ2 as an antibody having the sequence set forth in SEQ ID NO:5 or binds the same epitope on human Vδ2 as an antibody having the sequence set forth in SEQ ID NO:20.

In one embodiment of the multispecific antibody of the invention, the second antigen-binding region comprises the VH CDR1 sequence set forth in SEQ ID NO:17, the VH CDR2 sequence set forth in SEQ ID NO:18 and the VH CDR3 sequence set forth in SEQ ID NO:19 or comprises the VH CDR1 sequence set forth in SEQ ID NO:21, the VH CDR2 sequence set forth in SEQ ID NO:22 and the VH CDR3 sequence set forth in SEQ ID NO:23.

In one embodiment of the multispecific antibody of the invention, the second antigen-binding region is humanized.

In a further embodiment, the second antigen-binding region comprises or consists of
 (a) the sequence set forth in SEQ ID NO:5, or
 (b) a sequence having at least 90%, such as least 92%, e.g. at least 94%, such as at least 96%, e.g. at least 98% sequence identity to the sequence set forth in SEQ ID NO:5.

In one embodiment of the multispecific antibody of the invention, the first antigen-binding region comprises the VH CDR1 sequence set forth in SEQ ID NO:14, the VH CDR2 sequence set forth in SEQ ID NO:15 and the VH CDR3 sequence set forth in SEQ ID NO:16 and wherein the second antigen-binding region comprises the VH CDR1 sequence set forth in SEQ ID NO:17, the VH CDR2 sequence set forth in SEQ ID NO:18 and the VH CDR3 sequence set forth in SEQ ID NO:19.

In another embodiment of the multispecific antibody of the invention, the first antigen-binding region comprises the VH CDR1 sequence set forth in SEQ ID NO:14, the VH CDR2 sequence set forth in SEQ ID NO:15 and the VH CDR3 sequence set forth in SEQ ID NO:16 and wherein the second antigen-binding region comprises the VH CDR1 sequence set forth in SEQ ID NO:21, the VH CDR2 sequence set forth in SEQ ID NO:22 and the VH CDR3 sequence set forth in SEQ ID NO:23.

In one embodiment, the multispecific antibody of the invention is capable of mediating killing of PSMA-expressing cells, e.g. LNCaP cells, 22Rv1 cells or VCaP cells through activation of Vγ9Vδ2 T cells. Preferably, the antibody is capable of inducing killing of LNCaP cells through activation of Vγ9Vδ2 T cells with an EC50 value of 50 pM or less, such as 25 pM or less, e.g. 20 pM or less, such as 15 pM or less, e.g. 10 pM or less, or even 5 pM or less, such as 2 pM or less or 1 pM or less when tested as described in Example 6 herein.

In another embodiment, the antibody is capable of inducing killing of LNCaP, 22Rv1 or VCaP cells through activation of Vγ9Vδ2 T cells with an EC50 value of 50 PM or less, such as 25 pM or less, e.g. 20 pM or less, such as 15 pM or less when tested after 24 hours as described in Example 13 herein, preferably both at a 1:1 and a 1:10 effector to target cell ratio.

In another embodiment, the multispecific antibody of the invention is capable of binding to the PSMA positive prostate cancer cell line LNCaP with an EC50 of 50 nM or less, such as 20 nM or less, e.g. 10 nM of less, when tested as described in Example 7 herein. In another embodiment, the multispecific antibody of the invention is capable of binding to Vγ9Vδ2 T cells with an EC50 of 10 nM or less, such as 5 nM or less, e.g. 2 nM of less, when tested as described in Example 7 herein. In another embodiment, the multispecific antibody of the invention is capable of binding to recombinant human PSMA protein with a KD value of 100 nM or less, such as 50 nM or less, when tested as described in Example 11 herein. In another embodiment, the multispecific antibody of the invention is capable of binding to human Vγ9Vδ2-Fc with a KD value of 10 nM or less, such as 5 nM or less, e.g. 2 nM or less, such as 1 nM or less when tested as described in Example 11 herein.

In a further embodiment, the multispecific antibody is capable of mediating killing of human PSMA-expressing cells from a prostate cancer patient. Killing of human PSMA-expressing cells from a prostate cancer patient may e.g. be determined as described in Example 10 herein. In one embodiment, the multispecific antibody of the invention is capable of mediating specific cell death of more than 25%, such as more than 50%, at a concentration of 50 nM, as determined in the assays described in Example 10 or Example 14 herein.

In a further embodiment, the multispecific antibody is not capable of mediating killing of PSMA-negative cells, such as PSMA negative human cells. In another embodiment, the multispecific antibody does not induce IL-2, IL-4, IL-6, IL-10 or TNFα in whole blood from healthy donors at concentrations up to 280 nM, when tested as described in Example 16 herein. In another embodiment, the multispecific antibody induces more than 10-fold less IL-8 and/or more than 50-fold less IFNα than Campath® in whole blood from healthy donors when tested as described in Example 16 herein.

In one embodiment, the first antigen-binding region and the second antigen-binding region are covalently linked to each other via a peptide linker, e.g. a linker having a length of from 1 to 20 amino acids, e.g. from 1 to 10 amino acids, such as 2, 3, 4, 5, 6, 7, 8 or 10 amino acids. In one embodiment, the peptide linker comprises or consists of the sequence GGGGS, set forth in SEQ ID NO:6.

In some embodiments, the first antigen-binding region capable of binding human PSMA is located N-terminally of the second antigen-binding region capable of binding a human Vγ9Vδ2 T cell receptor.

In one embodiment of the invention, the multispecific antibody further comprises a half-life extension domain. In one embodiment, the multispecific antibody has a terminal half-life that is longer than about 168 hours when administered to a human subject. Most preferably the terminal half-life is 336 hours or longer. The "terminal half-life" of an antibody, when used herein refers to the time taken for the serum concentration of the polypeptide to be reduced by 50%, in vivo in the final phase of elimination.

In one embodiment, the multispecific antibody comprises an Fc region. Various method for making bispecific antibodies have been described in the art, e.g. reviewed by Brinkmann and Kontermann (2017) MAbs 9:182. In one embodiment of the present invention, the Fc region is a heterodimer comprising two Fc polypeptides, wherein the first antigen-binding region is fused to the first Fc polypeptide and the second antigen-binding region is fused to the second Fc polypeptide and wherein the first and second Fc polypeptides comprise asymmetric amino acid mutations that favor the formation of heterodimers over the formation of homodimers (see e.g. Ridgway et al. (1996) 'Knobs-into-holes' engineering of antibody CH3 domains for heavy chain heterodimerization. Protein Eng 9:617). In a further embodiment hereof, the CH3 regions of the Fc polypeptides comprise said asymmetric amino acid mutations, preferably the first Fc polypeptide comprises a T366W substitution and the second Fc polypeptide comprises T366S, L368A and Y407V substitutions, or vice versa, wherein the amino acid positions correspond to human IgG1 according to the EU numbering system. In a further embodiment, the cysteine residues at position 220 in the first and second Fc polypeptides have been deleted or substituted, wherein the amino acid position corresponds to human IgG1 according to the EU numbering system. In a further embodiment, the region comprises the sequence set forth in SEQ ID NO:10.

In some embodiments, the first and/or second Fc polypeptides contain mutations that render the antibody inert, i.e. unable to mediate effector functions. In one embodiment, the first and second Fc polypeptides comprise a mutation at position 234 and/or 235, preferably the first and second Fc polypeptide comprise an L234F and an L235E substitution, wherein the amino acid positions correspond to human IgG1 according to the EU numbering system.

In a preferred embodiment, the first antigen-binding region comprises the sequence set forth in SEQ ID NO:2, the second antigen-binding region comprises the sequence set forth in SEQ ID NO:5 and
  (a) the first Fc polypeptide comprises the sequence set forth in SEQ ID NO:12 and the second Fc polypeptide comprises the sequence set forth in SEQ ID NO:13, or
  (b) the first Fc polypeptide comprises the sequence set forth in SEQ ID NO:12 and the second Fc polypeptide comprises the sequence set forth in SEQ ID NO:13.

In a further embodiment, the antibody comprises or consists of the sequences set forth in SEQ ID NO:25 and SEQ ID NO:26.

In a further main aspect, the invention relates to a pharmaceutical composition comprising a multispecific antibody according to the invention as described herein and a pharmaceutically-acceptable excipient.

Antibodies may be formulated with pharmaceutically-acceptable excipients in accordance with conventional techniques such as those disclosed in (Rowe et al., Handbook of Pharmaceutical Excipients, 2012 June, ISBN 9780857110275). The pharmaceutically-acceptable excipient as well as any other carriers, diluents or adjuvants should be suitable for the antibodies and the chosen mode of administration. Suitability for excipients and other components of pharmaceutical compositions is determined based on the lack of significant negative impact on the desired biological properties of the chosen antibody or pharmaceutical composition of the present invention (e.g., less than a substantial impact (10% or less relative inhibition, 5% or less relative inhibition, etc.) upon antigen binding).

A pharmaceutical composition may include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition. Further pharmaceutically-acceptable excipients include any and all suitable solvents, dispersion media, coatings, antibacterial and antifungal agents, isotonicity agents, antioxidants and absorption-delaying agents and the like that are physiologically compatible with an antibody of the present invention.

In one embodiment, the pharmaceutical composition comprises a multispecific antibody of the invention (preferably an antibody comprising an Fc region), a buffer and an antioxidant, wherein the pH of the composition is between 5.4 and 7.4, such as between 5.4 and 6.1.

In a further embodiment, the pharmaceutical composition comprises a multispecific antibody of the invention, a buffer and methionine, wherein the pH of the composition is between 5.4 and 7.4, such as between 5.4 and 6.1.

In a further embodiment, the pharmaceutical composition comprises a multispecific antibody of the invention, a buffer, sucrose, polysorbate 80 and methionine, wherein the pH of the composition is between 5.4 and 7.4, such as between 5.4 and 6.1.

In a further embodiment, the pharmaceutical composition comprises a multispecific antibody of the invention, a histidine or sodium acetate buffer, sucrose, polysorbate 80 and methionine, wherein the pH of the composition is between 5.4 and 7.4, such as between 5.4 and 6.1.

Preferably, the buffer concentration is between 5 and 25 mM, such as 10 mM. Preferably, the sucrose concentration is between 100 and 500 mM, such as between 250 mM and 300 mM, e.g. 280 mM. Preferably, the polysorbate 80 concentration is between 0.005% and 0.1%, such between 0.01% and 0.05%, e.g. 0.02%. Preferably, the methionine concentration is between 0.2 mM and 5 mM, such between 0.5 mM and 2 mM, e.g. 1 mM. Preferably, the multispecific antibody in the composition comprises an Fc region.

Thus, in a preferred embodiment, the pharmaceutical composition comprises a multispecific antibody of the invention comprising an Fc region, a histidine or sodium acetate buffer, sucrose, polysorbate 80 and methionine, wherein the pH of the composition is between 5.4 and 7.4, such as between 5.4 and 6.1.

Thus, in a further preferred embodiment, the pharmaceutical composition comprises a multispecific antibody of the invention comprising an Fc region, a 10 M histidine or sodium acetate buffer, 280 mM sucrose, 0.02% polysorbate 80 and 1 mM methionine, wherein the pH of the composition is 5.5 or 6.0.

Preferably, such as Fc region is a heterodimer comprising two Fc polypeptides, wherein the first antigen-binding region is fused to the first Fc polypeptide and the second antigen-binding region is fused to the second Fc polypeptide and wherein the first and second Fc polypeptides comprise asymmetric amino acid mutations that favor the formation of heterodimers over the formation of homodimers. Preferably, the CH3 regions of the Fc polypeptides comprise said asymmetric amino acid mutations, wherein preferably the first Fc polypeptide comprises a T366W substitution and the second Fc polypeptide comprises T366S, L368A and Y407V substitutions, or vice versa. Furthermore, preferably, the cysteine residues at position 220 in the first and second Fc polypeptides have been deleted or substituted and/or the first and second Fc polypeptides further comprise a mutation at position 234 and/or 235, wherein preferably the first and second Fc polypeptide comprise an L234F and an L235E substitution.

Furthermore, preferably, the multispecific antibody in the composition comprises a first antigen-binding region comprising the sequence set forth in SEQ ID NO:2, a second antigen-binding region comprising the sequence set forth in SEQ ID NO:5 and
 (a) the first Fc polypeptide comprises the sequence set forth in SEQ ID NO:12 and the second Fc polypeptide comprises the sequence set forth in SEQ ID NO:13, or
 (b) the first Fc polypeptide comprises the sequence set forth in SEQ ID NO:12 and the second Fc polypeptide comprises the sequence set forth in SEQ ID NO:13
 and the pharmaceutical composition comprises a 10 M histidine or sodium acetate buffer, 280 mM sucrose, 0.02% polysorbate 80 and 1 mM methionine, wherein the pH of the composition is 5.5 or 6.0. Preferably, the antibody concentration is between 0.1 mg/mL and 20 mg/mL, such as between 0.1 and 10 mg/ml, for example between 0.5 mg/mL and 2 mg/ml, such as 1 mg/mL.

In a further main aspect, the invention relates to the multispecific antibody according to the invention as described herein for use as a medicament.

A multispecific antibody according to the invention enables creating a microenvironment that is beneficial for killing of tumor cells, in particular PSMA-positive tumor cells, by Vγ9Vδ2 T cells.

Accordingly, in a preferred embodiment, the multispecific antibody is for use in the treatment of cancer. In a further preferred embodiment, the multispecific antibody is for use in the treatment of prostate cancer, such as metastatic or non-metastatic prostate cancer. In another embodiment, the multispecific antibody is for use in the treatment of cancers in which PSMA is expressed on the tumor neo-vasculature or tumor-associated endothelial cells of primary or metastatic tumors including from colorectal cancer, lung cancer, breast cancer, endometrial and ovarian cancer, gastric cancer, renal cell cancer, urothelial cancer, hepatocellular cancer, oral squamous cancer, thyroid tumors and glioblastomas. In another embodiment, the multispecific antibody is for use in the treatment of adenoid cystic carcinoma of the head and neck.

Similarly, the invention relates to a method of treating a disease comprising administration of a multispecific antibody according to the invention as described herein to a human subject in need thereof. In one embodiment, the disease is cancer, such as prostate cancer, e.g. metastatic or non-metastatic prostate cancer.

In some embodiments, the antibody is administered as monotherapy. However, antibodies of the present invention may also be administered in combination therapy, i.e., combined with other therapeutic agents relevant for the disease or condition to be treated.

"Treatment" or "treating" refers to the administration of an effective amount of an antibody according to the present invention with the purpose of easing, ameliorating, arresting, eradicating (curing) or preventing symptoms or disease states. An "effective amount" refers to an amount effective, at dosages and for periods of time necessary, to achieve a desired therapeutic result. An effective amount of a polypeptide, such as an antibody, may vary according to factors such as the disease stage, age, sex, and weight of the individual, and the ability of the antibody to elicit a desired response in the individual. An effective amount is also one in which any toxic or detrimental effects of the antibody are outweighed by the therapeutically beneficial effects. An exemplary, non-limiting range for an effective amount of an antibody of the present invention is about 0.1 mg/kg to 100 mg/kg, such as about 1 mg/kg to 50 mg/kg, for example about 0.01 to 20 mg/kg, such as about 0.1 to 10 mg/kg, for instance about 0.5, about 0.3, about 1, about 3, about 5, or about 8 mg/kg. Administration may be carried out by any suitable route, but will typically be parenteral, such as intravenous, intramuscular or subcutaneous.

Multispecific antibodies of the invention are typically produced recombinantly, i.e. by expression of nucleic acid constructs encoding the antibodies in suitable host cells, followed by purification of the produced recombinant antibody from the cell culture. Nucleic acid constructs can be produced by standard molecular biological techniques well-known in the art. The constructs are typically introduced into the host cell using an expression vector. Suitable nucleic acid constructs and expression vectors are known in the art. Host cells suitable for the recombinant expression of antibodies are well-known in the art, and include CHO, HEK-293, Expi293F, PER-C6, NS/0 and Sp2/0 cells.

Accordingly, in a further aspect, the invention relates to a nucleic acid construct encoding a multispecific antibody according to the invention. In one embodiment, the construct is a DNA construct. In another embodiment, the construct is an RNA construct.

In a further aspect, the invention relates to an expression vector comprising a nucleic acid construct encoding a multispecific antibody according to the invention.

In a further aspect, the invention relates to a host cell, i.e. a recombinant host cell, such as a mammalian host cell, preferably a CHO cell comprising one or more nucleic acid constructs encoding a multispecific antibody according to the invention or an expression vector comprising a nucleic acid construct encoding a multispecific antibody according to the invention.

Accordingly, in a further aspect, the invention relates to production of a multispecific antibody of the invention, preferably a multispecific antibody of the invention comprising an Fc region, by (co-) expression of one or more nucleic acid constructs encoding the multispecific antibody in a suitable host cell, such as a mammalian host cell, e.g. a CHO cell, followed by purification of the produced recombinant antibody from the cell culture or the supernatant after removal of the cells.

TABLE 1

Sequence listing.

| SEQ ID.code | Description | Sequence |
|---|---|---|
| 1 | LV1044-JVZ007 VHH | EVQLVESGGGLVQPGGSLTLSCAASRFMISEYSMH WVRQAPGKGLEWVSTINPAGTTDYAESVKGRFTIS RDNAKNTLYLQMNSLKPEDTAVYYCDGYGYRGQG TQVSS |
| 2 | LV1050 VHH | EVQLVESGGGLVQPGGSLRLSCAASRFMISEYSMH WVRQAPGKGLEWVSTINPAGTTDYADSVKGRFTI SRDNAKNTLYLQMNSLRAEDTAVYYCDGYGYRGQ GTQVTVSS |
| 3 | LV1051 VHH | EVQLVESGGGSVQPGGSLRLSCAASRFMISEYSM HWVRQAPGKGLEWVSTINPAGTTDYADSVKGRFT ISRDNAKNTLYLQMNSLRAEDTAVYYCDGYGYRGL GTQVTVSS |
| 4 | 5C8 VHH | EVQLVESGGGLVQAGGSLRLSCAASGRPFSNYAM GWFRQAPGKEREFVAAISWSGGSTSYADSVKGRF TISRDNAKNTVYLQMNSPKPEDTAIYYCAAQFSGA DYGFGRLGIRGYEYDYWGQGTQVTVSS |
| 5 | 5C8var1 VHH | EVQLLESGGGSVQPGGSLRLSCAASGRPFSNYAM SWFRQAPGKEREFVSAISWSGGSTSYADSVKGRF TISRDNSKNTLYLQMNSLRAEDTAVYYCAAQFSGA DYGFGRLGIRGYEYDYWGQGTQVTVSS |
| 6 | linker | GGGGS |
| 7 | LV1044-5C8 Bispecific Ab | EVQLVESGGGLVQPGGSLTLSCAASRFMISEYSMH WVRQAPGKGLEWVSTINPAGTTDYAESVKGRFTIS RDNAKNTLYLQMNSLKPEDTAVYYCDGYGYRGQG TQVTVSSGGGGSEVQLVESGGGLVQAGGSLRLSC AASGRPFSNYAMGWFRQAPGKEREFVAAISWSGG STSYADSVKGRFTISRDNAKNTVYLQMNSPKPEDT AIYYCAAQFSGADYGFGRLGIRGYEYDYWGQGTQ VTVSS |
| 8 | LV1050-5C8var1 Bispecific Ab | EVQLVESGGGLVQPGGSLRLSCAASRFMISEYSMH WVRQAPGKGLEWVSTINPAGTTDYADSVKGRFTI SRDNAKNTLYLQMNSLRAEDTAVYYCDGYGYRGQ GTQVTVSSGGGGSEVQLLESGGGSVQPGGSLRLS CAASGRPFSNYAMSWFRQAPGKEREFVSAISWSG GSTSYADSVKGRFTISRDNSKNTLYLQMNSLRAED TAVYYCAAQFSGADYGFGRLGIRGYEYDYWGQGT QVTVSSAAAEPEA |
| 9 | LV1051-5C8var1 Bispecific Ab | EVQLVESGGGSVQPGGSLRLSCAASRFMISEYSM HWVRQAPGKGLEWVSTINPAGTTDYADSVKGRFT ISRDNAKNTLYLQMNSLRAEDTAVYYCDGYGYRGL GTQVTVSSGGGGSEVQLLESGGGSVQPGGSLRLS CAASGRPFSNYAMSWFRQAPGKEREFVSAISWSG GSTSYADSVKGRFTISRDNSKNTLYLQMNSLRAED TAVYYCAAQFSGADYGFGRLGIRGYEYDYWGQGT QVTVSSAAAEPEA |
| 10 | Modified hinge region sequence | AAASDKTHTCPPCP |
| 11 | wtIgG1 (G1m17, G1m(z) allotype) | CH2 and CH3 | APELLGGPSVFLFPPKPKDTLMISRTPEVTCVVVDV SHEDPEVKFNWYVDGVEVHNAKTKPREEQYNSTY RVVSVLTVLHQDWLNGKEYKCKVSNKALPAPIEKT ISKAKGQPREPQVYTLPPSRDELTKNQVSLTCLVK GFYPSDIAVEWESNGQPENNYKTTPPVLDSDGSFF LYSKLTVDKSRWQQGNVFSCSVMHEALHNHYTQ KSLSLSPG |
| 12 | IgG1 L234F L235E T366W | Heavy chain region constant variant | AAASDKTHTCPPCPAPEFEGGPSVFLFPPKPKDTLM ISRTPEVTCVVVDVSHEDPEVKFNWYVDGVEVHN AKTKPREEQYNSTYRVVSVLTVLHQDWLNGKEYK CKVSNKALPAPIEKTISKAKGQPREPQVYTLPPSRD ELTKNQVSLWCLVKGFYPSDIAVEWESNGQPENN YKTTPPVLDSDGSFFLYSKLTVDKSRWQQGNVFSC SVMHEALHNHYTQKSLSLSPG |

TABLE 1-continued

Sequence listing.

| SEQ ID.code | Description | Sequence |
|---|---|---|
| 13 | IgG1 L234F L235E T366S L368A Y407V | Heavy chain constant region variant | AAASDKTHTCPPCPAPEFEGGPSVFLFPPKPKDTLM ISRTPEVTCVVVDVSHEDPEVKFNWYVDGVEVHN AKTKPREEQYNSTYRVVSVLTVLHQDWLNGKEYK CKVSNKALPAPIEKTISKAKGQPREPQVYTLPPSRD ELTKNQVSLSCAVKGFYPSDIAVEWESNGQPENN YKTTPPVLDSDGSFFLVSKLTVDKSRWQQGNVFS CSVMHEALHNHYTQKSLSLSPG |
| 14 | LV1050 | CDR1 | RFMISEYSMH |
| 15 | LV1050 | CDR2 | TINPAGTTDYADSVKG |
| 16 | LV1050 | CDR3 | DGYGY |
| 17 | 5C8var1 | CDR1 | NYAMS |
| 18 | 5C8var1 | CDR2 | AISWSGGSTSYADSVKG |
| 19 | 5C8var1 | CDR3 | QFSGADYGFGRLGIRGYEYDY |
| 20 | 6H4 | VHH | EVQLVESGGGLVQAGGSLRLSCAASGRPFSNYGM GWFRQAPGKKREFVAGISWSGGSTDYADSVKGR FTISRDNAKNTVYLQMNSLKPEDTAVYYCAAVFSG AETAYYPSDDYDYWGQGTQVTVSS |
| 21 | 6H4 | CDR1 | GRPFSNYGMG |
| 22 | 6H4 | CDR2 | GISWSGGSTDYADSVKG |
| 23 | 6H4 | CDR3 | VFSGAETAYYPSDDYDY |
| 24 | PSMA | | MWNLLHETDSAVATARRPRWLCAGALVLAGGFFLL GFLFGWFIKSSNEATNITPKHNMKAFLDELKAENIK KFLYNFTQIPHLAGTEQNFQLAKQIQSQWKEFGLD SVELAHYDVLLSYPNKTHPNYISIINEDGNEIFNTSL FEPPPPGYENVSDIVPPFSAFSPQGMPEGDLVYVNY ARTEDFFKLERDMKINCSGKIVIARYGKVFRGNKV KNAQLAGAKGVILYSDPADYFAPGVKSYPDGWNLP GGGVQRGNILNLNGAGDPLTPGYPANEYAYRRGIA EAVGLPSIPVHPIGYYDAQKLLEKMGGSAPPDSSW RGSLKVPYNVGPGFTGNFSTQKVKMHIHSTNEVT RIYNVIGTLRGAVEPDRYVILGGHRDSWVFGGIDP QSGAAVVHEIVRSFGTLKKEGWRPRRTILFASWDA EEFGLLGSTEWAEENSRLLQERGVAYINADSSIEG NYTLRVDCTPLMYSLVHNLTKELKSPDEGFEGKSLY ESWTKKSPSPEFSGMPRISKLGSGNDFEVFFQRLG IASGRARYTKNWETNKFSGYPLYHSVYETYELVEKF YDPMFKYHLTVAQVRGGMVFELANSIVLPFDCRDY AVVLRKYADKIYSISMKHPQEMKTYSVSFDSLFSA VKNFTEIASKFSERLQDFDKSNPIVLRMMNDQLMF LERAFIDPLGLPDRPFYRHVIYAPSSHNKYAGESFP GIYDALFDIESKVDPSKAWGEVKRQIYVAAFTVQA AAETLSEVA |
| 25 | 5C8var1 Fc L234F L235E T366W | | EVQLLESGGGSVQPGGSLRLSCAASGRPFSNYAM SWFRQAPGKEREFVSAISWSGGSTSYADSVKGRF TISRDNSKNTLYLQMNSLRAEDTAVYYCAAQFSGA DYGFGRLGIRGYEYDYWGQGTQVTVSSAAASDKT HTCPPCPAPEFEGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLWCLVKGFYPSDIAVEWESNGQPENNYKTTPPVL DSDGSFFLYSKLTVDKSRWQQGNVFSCSVMHEAL HNHYTQKSLSLSPG |
| 26 | LV1050 Fc L234F L235E T366S L368A Y407V | | EVQLVESGGGLVQPGGSLRLSCAASRFMISEYSMH WVRQAPGKGLEWVSTINPAGTTDYADSVKGRFTI SRDNAKNTLYLQMNSLRAEDTAVYYCDGYGYRGQ GTQVTVSSAAASDKTHTCPPCPAPEFEGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSRDELTKNQVSLSCAVKGFYPSDIAVEWE |

TABLE 1-continued

Sequence listing.

| SEQ ID.code | Description | Sequence |
|---|---|---|
| | | SNGQPENNYKTTPPVLDSDGSFFLVSKLTVDKSRW QQGNVFSCSVMHEALHNHYTQKSLSLSPG |
| 27 | 5C8var1 Fc L234F L235E T366W | EVQLLESGGGSVQPGGSLRLSCAASGRPFSNYAM SWFRQAPGKEREFVSAISWSGGSTSYADSVKGRF TISRDNSKNTLYLQMNSLRAEDTAVYYCAAQFSGA DYGFGRLGIRGYEYDYWGQGTQVTVSSAAASDKT HTCPPCPAPEFEGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLWCLVKGFYPSDIAVEWESNGQPENNYKTTPPVL DSDGSFFLYSKLTVDKSRWQQGNVFSCSVMHEAL HNHYTQKSLSLSPGK |
| 28 | LV1050 Fc L234F L235E T366S L368A Y407V | EVQLVESGGGLVQPGGSLRLSCAASRFMISEYSMH WVRQAPGKGLEWVSTINPAGTTDYADSVKGRFTI SRDNAKNTLYLQMNSLRAEDTAVYYCDGYGYRGQ GTQVTVSSAAASDKTHTCPPCPAPEFEGGPSVFLF PPKPKDTLMISRTPEVTCVVVDVSHEDPEVKFNWY VDGVEVHNAKTKPREEQYNSTYRVVSVLTVLHQD WLNGKEYKCKVSNKALPAPIEKTISKAKGQPREPQ VYTLPPSRDELTKNQVSLSCAVKGFYPSDIAVEWE SNGQPENNYKTTPPVLDSDGSFFLVSKLTVDKSRW QQGNVFSCSVMHEALHNHYTQKSLSLSPGK |
| 29 | LV1050- 5C8var1- no-c-tag | EVQLVESGGGLVQPGGSLRLSCAASRFMISEYSMH WVRQAPGKGLEWVSTINPAGTTDYADSVKGRFTI SRDNAKNTLYLQMNSLRAEDTAVYYCDGYGYRGQ GTQVTVSSGGGGSEVQLLESGGGSVQPGGSLRLS CAASGRPFSNYAMSWFRQAPGKEREFVSAISWSG GSTSYADSVKGRFTISRDNSKNTLYLQMNSLRAED TAVYYCAAQFSGADYGFGRLGIRGYEYDYWGQGT QVTVSS |
| 30 | PSMA var | MARPLCTLLLLMATLAGALAGSHHHHHHGSKSSN EATNITPKHNMKAFLDELKAENIKKFLYNFTQIPHLA GTEQNFQLAKQIQSQWKEFGLDSVELAHYDVLLS YPNKTHPNYISIINEDGNEIFNTSLFEPPPPGYENVS DIVPPFSAFSPQGMPEGDLVYVNYARTEDFFKLERD MKINCSGKIVIARYGKVFRGNKVKNAQLAGAKGVI LYSDPADYFAPGVKSYPDGWNLPGGGVQRGNILN LNGAGDPLTPGYPANEYAYRRGIAEAVGLPSIPVHP IGYYDAQKLLEKMGGSAPPDSSWRGSLKVPYNVG PGFTGNFSTQKVKMHIHSTNEVTRIYNVIGTLRGA VEPDRYVILGGHRDSWVFGGIDPQSGAAVVHEIV RSFGTLKKEGWRPRRTILFASWDAEEFGLLGSTEW AEENSRLLQERGVAYINADSSIEGNYTLRVDCTPL MYSLVHNLTKELKSPDEGFEGKSLYESWTKKSPSP EFSGMPRISKLGSGNDFEVFFQRLGIASGRARYTK NWETNKFSGYPLYHSVYETYELVEKFYDPMFKYHLT VAQVRGGMVFELANSIVLPFDCRDYAVVLRKYADK IYSISMKHPQEMKTYSVSFDSLFSAVKNFTEIASKF SERLQDFDKSNPIVLRMMNDQLMFLERAFIDPLGL PDRPFYRHVIYAPSSHNKYAGESFPGIYDALFDIES KVDPSKAWGEVKRQIYVAAFTVQAAAETLSEVA |
| 31 | huVdelta2 ECD- Fc (hole)- His | MQRISSLIHLSLFWAGVMSAIELVPEHQTVPVSIGV PATLRCSMKGEAIGNYYINWYRKTQGNTMTFIYRE KDIYGPGFKDNFQGDIDIAKNLAVLKILAPSERDEG SYYCACDTLGMGGEYTDKLIFGKGTRVTVEPRSQP HTKPSVFVMKNGTNVACLVKEFYPKDIRINLVSSKK ITEFDPAIVISPSGKYNAVKLGKYEDSNSVTCSVQH DNKTVHSTDFEVKTDSTDHVKPKETENTKQPSKS CHKPKAIVHTEKVNMMSLTAAASDKTHTCPPCPAP ELLGGPSVFLFPPKPKDTLMISRTPEVTCVVVDVSH EDPEVKFNWYVDGVEVHNAKTKPREEQYNSTYRV VSVLTVLHQDWLNGKEYKCKVSNKALPAPIEKTIS KAKGQPREPQVYTLPPSRDELTKNQVSLSCAVKGF YPSDIAVEWESNGQPENNYKTTPPVLDSDGSFFLV SKLTVDKSRWQQGNVFSCSVMHEALHNHYTQKS LSLSPGHHHHHH |

TABLE 1-continued

Sequence listing.

| SEQ ID.code | Description | Sequence |
|---|---|---|
| 32 | huVgamma9 ECD-Fc (knob)- C-tag | MLSLLHASTLAVLGALCVYGAGHLEQPQISSTKTLS KTARLECVVSGITISATSVYWYRERPGEVIQFLVSI SYDGTVRKESGIPSGKFEVDRIPETSTSTLTIHNVE KQDIATYYCALWEAQQELGKKIKVFGPGTKLIITDK QLDADVSPKPTIFLPSIAETKLQKAGTYLCLLEKFFP DVIKIHWEEKKSNTILGSQEGNTMKTNDTYMKFS WLTVPEKSLDKEHRCIVRHENNKNGVDQEIIFPPIK TDVITMDPKDNCSKDANDTLLLQLTNTSAAAASDK THTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLWCLVKGFYPSDIAVEWESNGQPENNYKTTPPVL DSDGSFFLYSKLTVDKSRWQQGNVFSCSVMHEAL HNHYTQKSLSLSPGAAAEPEA |

EXAMPLES

Example 1: PBMC Isolation and Generation of Human Donor-Derived Vγ9Vδ2-T Cell Cultures Whole blood was collected from healthy donor volunteers. Alternatively, buffy coats were obtained from blood supply service Sanquin and used for isolation of peripheral blood mononuclear cells (PBMC). PBMC were isolated using Lymphoprep™ density gradient centrifugation. Vγ9Vδ2-T cells were then isolated from healthy donor PBMC by magnetic-activated cell sorting (MACS) using a FITC-labeled anti-TCR Vδ2 mouse monoclonal antibody (Mab) in combination with goat anti-mouse IgG microbeads. Purified Vγ9Vδ2-T cells were stimulated every seven days with a feeder cell mix consisting of irradiated PBMC from two healthy donors and an Epstein Barr Virus transformed B cell line (JY) resuspended in Roswell Park Memorial Institute (RPMI) medium supplemented with 10 IU/mL IL-7, 10 ng/ml IL-15 and 50 ng/ml PHA. Expanded Vγ9Vδ2-T cell cultures were always tested for purity before being used for experiments and always found to be >95% Vγ9 and Vδ2 double positive.

Example 2: Humanization of the Anti-PSMA VHH JVZ-007 and Anti-Vγ9Vδ2 VHH 5C8

The amino acid sequence of the camelid-derived anti-PSMA VHH JVZ-007 (LV1044; SEQ ID NO:1) (J Nucl Med. 2015 July; 56(7):1094-9, supplemental data) was aligned to the human V gene database and the closest human germline match was found to be IGHV3-74*01. Based on sequence differences in the framework regions between the human and llama-derived sequence, two humanized variants (SEQ ID NO:2-3) were designed, see alignment in FIG. 1.

JVZ-007 and these two mutants were then combined with anti-Vγ9Vδ2 VHH 5C8 (a Vδ2 binding antibody described in WO2015156673) (SEQ ID NO:4) or 5C8var1, a humanized variant of 5C8 (SEQ ID NO:5), in bispecific VHH format: anti-PSMA VHH-linker-anti Vγ9Vδ2 VHH. The sequence of the linker was GGGGS (SEQ ID NO:6). A C-terminal C-tag (EPEA sequence) preceded by three alanine residues was in some constructs added for purification and detection purposes. The sequences of the resulting constructs are set forth in SEQ ID NO:7-9.

Example 3: Design of a Half-Life Extended Version of the Bispecific VHH Format

A half-life extended version of the bispecific VHH format was designed, based on an Fc-containing format. VHH sequences were coupled to a slightly modified human IgG1 hinge region: Amino acid residues 216-230 (EU numbering) were changed to AAASDKTHTCPPCP (SEQ ID NO:10). This omits the cysteine that normally bridges to the other heavy chain and replaces the 'EPK' upper hinge sequence with three alanines. This modified hinge was coupled to an IgG1 (G1m17, G1m(z) allotype sequence)-CH2 and -CH3 sequences (SEQ ID NO:11). The CH2 sequence was modified to contain Fc silencing mutations (L234F, L235E) and the CH3 sequence was modified to either contain a 'knob' mutation (T366W) (SEQ ID NO:12), or three mutations that create a 'hole' (T366S, L368A and Y407V) (SEQ ID NO:13). This knob-into-hole (KiH) technology induces the preferential hetero-dimerization of the two chains. The resulting construct is schematically depicted in FIG. 2.

Example 4: Cloning, Expression and Purification of Bispecific VHH Molecules and Fc-Containing Constructs Amino acid sequences of bispecific VHH molecules were reverse-translated to cDNA and then codon-optimized for expression in human cells. Regulatory elements were added: an N-terminal Kozak sequence and C-terminal stop codon (including BamH1 and Not1 restriction sites for cloning) and the cDNA was made as a synthetic gene. cDNAs were cloned into a suitable vector and their sequences were verified. Expression of the proteins was performed by transient transfection of the resulting plasmids in HEK293_E cells. Proteins were purified from the culture supernatant by means of protein-A affinity chromatography and preparative size-exclusion chromatography.

The amino acid sequences of the two protein chains of Fc-containing constructs were reverse-translated into the encoding cDNA, necessary regulatory elements were added (Kozak sequence, stop codon and cloning sites BamH1 and Not1) and the cDNAs were codon-optimized for expression. The cDNAs were made by synthetic gene synthesis and expression plasmids encoding either of the two protein chains were made by cloning the cDNAs separately into a suitable vector. The resulting plasmids were sequence-verified and then used to transfect CHO cells grown in suspension using different ratios of the two plasmids (1:2, 1:1 and 2:1). Secreted proteins were purified from the culture supernatant using protein-A affinity chromatography and were buffer-exchanged to PBS. Proteins were further purified by preparative size-exclusion chromatography.

Example 5: Testing of Humanization Variants of Anti-PSMA VHH JVZ-007

Purified bispecific VHHs containing the humanization variants were tested for their ability to induce target-dependent T cell activation in a 4-hour degranulation assay. Vγ9Vδ2 T cells were isolated from PBMC by means of magnetic activated cell sorting (MACS) and expanded as described in Example 1. Expanded Vγ9Vδ2 T cells used for experiments were always checked for purity and found to be >95% double positive for Vγ9- and Vδ2 staining in FACS. Purified, expanded Vγ9Vδ2 T cells were incubated with the same number of PSMA-positive LNCaP (ATCC, cat. Nr. CRL-1740) target cells (effector: target (E:T) cell ratio of 1:1) and a concentration range of bispecific construct. After 4 hours of incubation, the percentage of T cells expressing CD107a was determined by staining in FACS.

FIG. 3 shows that the humanization variants of the PSMA VHH JVZ-007 showed a strong potency in inducing Vγ9Vδ2 T cell degranulation dependent on the antigen-positive cell line LNCaP. However, a single high concentration of bispecific construct did not cause significant activation of T cells when the antigen-negative cell line PC-3 was used.

Example 6: Cytotoxicity Mediated by Bispecific VHH and Fc-Containing Counterpart The two VHH sequences of bispecific VHH LV1050-5C8var1 were re-formatted into a half-life extended molecule containing a human IgG1 Fc as described above, resulting in the constructs set forth in SEQ ID NO:25 and SEQ ID NO:26 (5C8var1-Fc and LV1050-Fc).

Both the bispecific VHH construct LV1050-5C8var1 and the Fc-containing counterpart 5C8var1-Fc×LV1050-Fc (also termed LV1050-Fc×5C8var1 herein) were tested for their ability to induce cytotoxicity of LNCaP cells through activation of Vγ9Vδ2 T cells.

Figure 4:
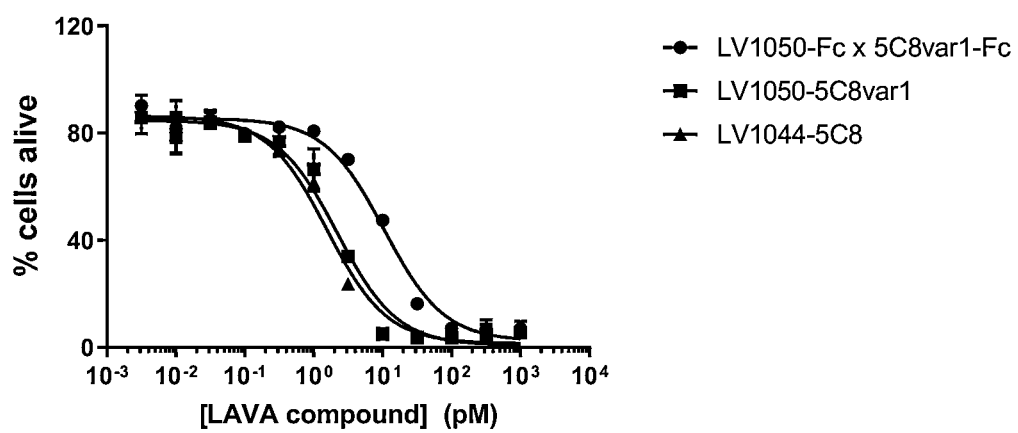
FIG. 4: Antibody induced-, Vγ9Vδ2 T cell mediated cytotoxicity of LNCaP cells.

FIG. 4 shows that both the bispecific VHH, as well as the Fc-containing counterpart containing the same VHH sequences were able to induce 100% tumor cell lysis after 24 hours in an E:T ratio of 1:1. The bispecific VHH LV1044-5C8 containing the original anti-PSMA VHH JVZ-007 was as potent as the humanized version LV1050-5C8var1 and both of these were slightly more potent than the Fc-containing counterpart 5C8var1-Fc×LV1050-Fc. EC50 values found were 2.2 pM and 1.6 pM for LV1050-5C8var1 and LV1044-5C8 respectively and 10.5 pM for 5C8var1-Fc× LV1050-Fc. For subsequent experiments, a C-terminal lysine was added for expression purposes to both constructs encoding Fc-containing chains resulting in the coding sequences set forth in SEQ ID NO:27 and SEQ ID NO:28. Analysis of the produced polypeptides revealed that the C-terminal lysines were clipped off (data not shown), thus resulting in identical polypeptides to those produced from constructs not encoding a C-terminal lysine.

Example 7: Binding of LV1050-Fc×5C8var1-Fc to Target Positive Cells in FACS

Bispecific Fc-containing construct 5C8var1-Fc×LV1050-Fc cloned, expressed and purified as described above. To test the binding of the molecule to PSMA, a concentration range of antibody was tested for binding to the PSMA positive prostate cancer cell line LNCaP and to the antigen negative cell line PC-3. Detection was performed with a polyclonal anti-human IgG antibody.

To test the binding of LV1050-Fc×5C8var1-Fc to Vγ9Vδ2 T cells, a concentration range of the compound (100 nM and a half-log dilution thereof) was tested for binding in FACS staining using detection with two different monoclonal antibodies directed towards VHH and (45H8 and 96A3F5; Genscript, cat. Nrs CP001/18L001614 and A01994 respectively).

FIG. 5 shows that the molecule binds specifically to PSMA (left panel), as it did not measurably stain the PSMA-negative cell line PC-3, but showed strong binding to LNCaP cells. The EC50 for binding was measured to be 7.3 nM. The affinity for the Vγ9Vδ2 TCR was measured to be 1.7 nM by FACS (right panel).

Example 8: Lead Bispecific Antibody LV1050-Fc×5C8var1-Fc Induces Potent Target-Dependent T Cell Activation and Target Cell Lysis To measure the potency of the bispecific T cell engager, target-positive LNCaP cells were incubated with a concentration range of the molecule and a fixed number of Vγ9Vδ2 T cells (effector: target ratio of 1:1). T cell activation was then measured by staining in FACS for CD107a expression on the T cells after four hours of incubation. Cytotoxicity was measured after 24 hours by measuring the number of viable cells in FACS (7AAD staining). FIG. 6 shows that LV1050-Fc×5C8var1-Fc induces potent T cell activation as witnessed by CD107a expression. In addition, this resulted in a strong cytotoxic effect on the LNCaP target cells. The EC50 values for cytotoxicity that were found were virtually the same for both bispecific VHH molecules tested (1.9 pM for LV1044-5C8 (produced without AAAEPEA tag in this experiment) and LV1050-5C8var1) and slightly higher for LV1050-Fc×5C8var1-Fc (9.4 pM).

Example 9: Frequency Vγ9Vδ2-T Cells and Expression of Ligands in Patient-Derived Tumor and Normal Tissue Prostate tumor tissue was obtained after radical prostatectomy from patients with non-metastatic prostate cancer. Both macroscopically normal tissue, as well as tumor tissue was analyzed. Tissue was cut into small pieces with a surgical blade and resuspended in dissociation medium composed of Iscove Modified Dulbecco Medium (IMDM) supplemented with 0.1% DNAse I (Roche), 0.14% Collagenase A, 100 IU/mL sodium penicillin/100 μg/mL streptomycin sulphate/2.0 mM L glutamine and 5% FCS. The tissue pieces were transferred to a sterile flask and incubated on a magnetic stirrer for 45 minutes at 37 degrees. After this incubation, the cell suspension was run through a 100 μM cell strainer. Tumor tissue was dissociated three times and normal tissue twice in total, after which cells were washed and prepared for viable cell count using trypan blue exclusion. Dissociated tumor—and normal tissues were analyzed for the presence of Vγ9Vδ2-T cells using staining in FACS with AF700 labeled anti-CD45 Mab, PerCP-Cy5.5 labeled anti-CD3 mAb, APC labeled anti-TCR Vγ9 mAb and BV711 labeled anti-TCR Vδ2 mAb. Expression of the targets EpCAM, PSMA and CD277 on tumor—and normal cells was determined using BV421 labeled anti-EpCAM Mab, FITC labeled anti-PSMA Mab and PE labeled anti-CD277 Mab.

FIG. 7 shows that there is a significant difference in both PSMA—as well as CD277 expression between tumor and normal tissue. Resected tissue was macroscopically examined and then defined as being tumor or normal tissue. This was then further corroborated by EpCAM positive staining for tumor in FACS, which correlated with PSMA expression. PSMA was almost absent from normal tissue and significantly expressed on dissociated tumour cells. CD277 (BTN3A) expression was also more highly expressed on tumour, although the difference lacked statistical significance. In contrast, the frequency of Vγ9Vδ2-T cells in both tumor-and normal tissue was largely comparable, with normal tissue having a slightly higher percentage.

Example 10: Functional Analysis of LV1044-5C8 Using Patient-Derived Target Cells To determine the potential of the bispecific constructs to mediate cytotoxicity Vγ9Vδ2-T cells against patient-derived target cells, dissociated tumor-and normal cell suspensions were incubated for 24 hours at 37° C. with or without 50 nM of compound and Vγ9Vδ2-T cell cultures in a 1:1 effector: target (E:T) ratio. The number of living target cells was determined using the life-death marker 7AAD and 123 count eBeads.

FIG. 8 shows that Vγ9Vδ2 T cells were capable of inducing tumor cell kill of patient-derived tumor cells in a target-and Vγ9Vδ2 T-cell dependent manner. Normal tissue that was largely devoid of PSMA expression was not affected by Vγ9Vδ2 T cells, even in the presence of 50 nM of bispecific antibody. However, PSMA-positive tumor cells were significantly killed after 24 hours, but only in the presence of both effector cells and bispecific antibody.

Example 11: Affinity Determination LV1050-Fcx5C8var1-Fc for Human PSMA and Vγ9Vδ2 TCR Using Biolayer Interferometry The affinities of LV1050-Fcx5C8var1-Fc for recombinant human PSMA and human Vγ9Vδ2 TCR were determined using biolayer interferometry (BLI). As ligand, 12.5 μg/mL biotinylated hPSMA or 5 μg/mL hVγ9Vδ2-Fc (consisting of SEQ ID NO:31 and 32) were loaded onto streptavidin biosensors. As analyte, two-fold serial dilutions of LV1050-Fcx5C8var1-Fc were used: ranging from 3.125 to 200 nM in combination with ligand hPSMA; ranging from 0.03125 to 20 nM in combination with ligand hVγ9Vδ2-Fc. As shown in the Table 2, LV1050-Fcx5C8var1-Fc binds with a $K_D$ value of 32±1.2 nM to human PSMA, and with a $K_D$ of 0.64±0.16 nM to the human Vγ9Vδ2 TCR.

Example 12: Epitope Mapping

To determine the epitope on PSMA bound by the VHH incorporated in LV1050-Fcx5C8var1-Fc, LV1050-5C8var1-no-c-tag (SEQ ID NO:29) (containing the identical PSMA binding VHH domain as LV1050-Fcx5C8var1-Fc) was used in the epitope mapping technology developed by CovalX AG (Pimenova et al. (2008) J Mass Spectrom 43:185). In short, a recombinant, PSMA protein (SEQ ID NO: 30) was allowed to bind to LV1050-5C8var1-no-c-tag, cross-linked, exposed to different proteases and the resulting peptides, cross-linked or not, were analyzed by high-resolution mass spectrometry.

Figure 9:
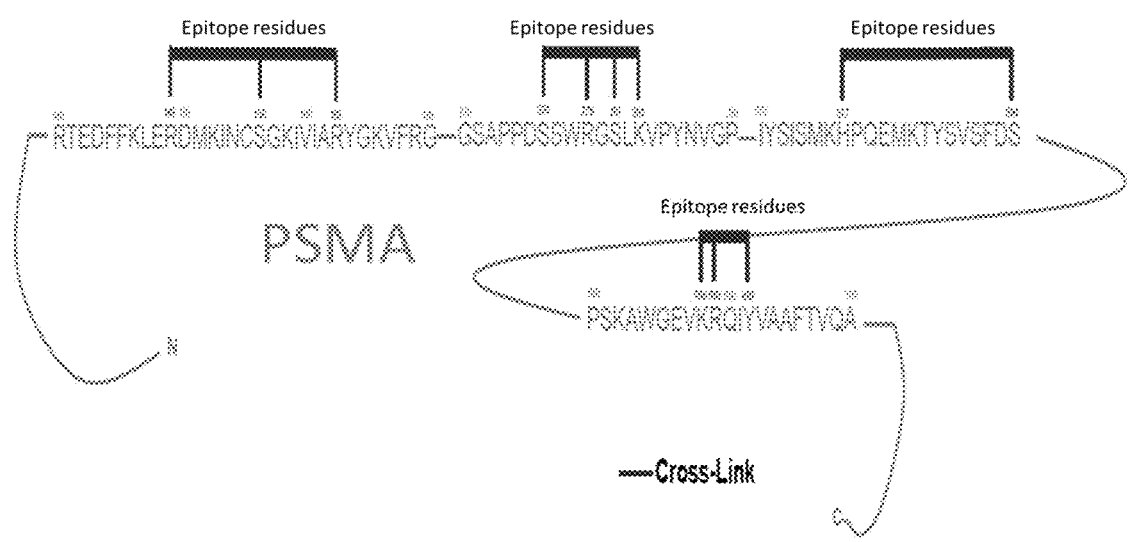
FIG. 9: Interaction mapped with crosslinks between PSMA and LV1050-5C8var1-no-C-tag. Numbers indicate the amino acid position in the PSMA construct with SEQ ID NO:30, which is based on UniProt ID Q04609, but with a different signal peptide. Position numbers in the PSMA construct correspond to the numbering in UniProt ID Q04609 as follows: Position in construct=position in UniProt ID Q04609+41. The PSMA fragments shown are set forth in SEQ ID NOs:33-36.

The results demonstrated the VHH to bind a conformational epitope which is shown in FIG. 9. The following residues were found to have a direct interaction with the antibody: R149, S156, R163, S276, R279, S281, K283, H577, S590, K688, R689 and Y692. These residues correspond to residues R190, S197, R204, S317, R320, S322, K324, H618, S631, K729, R730 and Y733 in UniProt sequence Q04609-1. None of the rare single nucleotide polymorphisms (SNPs) that have been identified in the FOLH1 gene were present in the epitope, suggesting LV1050-5C8var1-no-c-tag, and therefore LV1050-Fcx5C8var1-Fc, to be capable of binding all relevant identified SNP-variants of the target.

Figure 10:
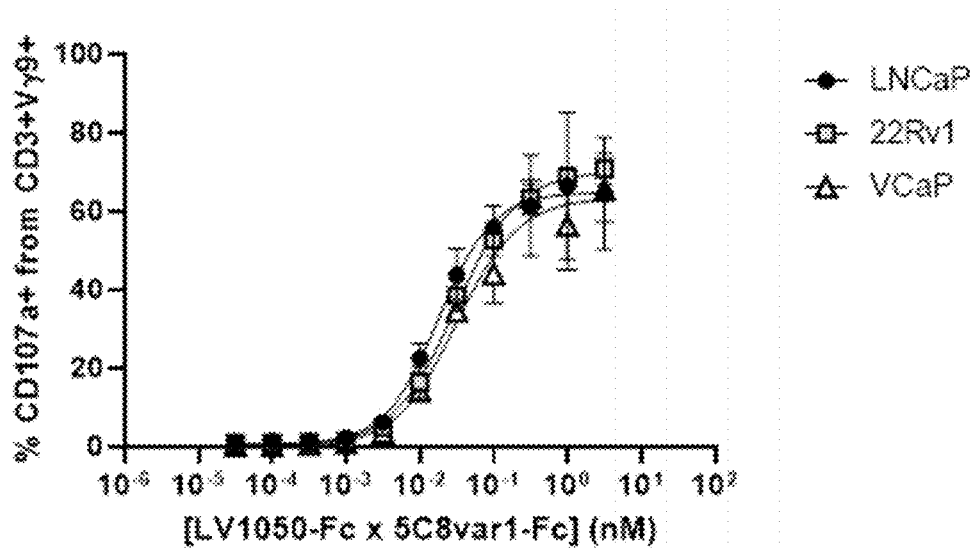
FIG. 10: Degranulation assay using expanded Vγ9Vδ2-T cells and PSMA positive tumor-derived cell lines. Degranulation was measured using primary, expanded Vγ9Vδ2-T cells co-cultured with different PSMA-expressing cell lines (LNCaP, 22Rv1 and VCaP cells). The percentage of CD107a positive (degranulating) cells in the CD3-Vγ9 gate is plotted as a function of the LV1050-Fc×5C8var1-Fc concentration.

Example 13: Further Functional Analysis of LV1050-Fcx5C8var1-Fc Using Tumor Derived Cell Lines The ability of LV1050-Fcx5C8var1-Fc to induce PSMA-dependent Vγ9Vδ2-T cell activation was determined in a 4-hour in vitro assay using expression of the degranulation marker CD107a (LAMP-1) as read-out. Expanded Vγ9Vδ2 T cells isolated from PBMCs from healthy donors were cultured with PSMA-expressing prostate-derived cancer cell lines LNCaP, VCaP or 22Rv1 in a 1:1 effector: target cell ratio, in the absence or presence of different concentrations of LV1050-Fcx5C8var1-Fc (ranging from 10 fM to 3.16 nM). Cells were harvested and the cell surface expression of CD107a was determined by flow cytometry. In the presence of all PSMA expressing tumor cell lines, LV1050-Fcx5C8var1-Fc induced very potent Vγ9Vδ2-T cell activation (FIG. 10) with $EC_{50}$ values in pM range (Table 3).

TABLE 2

Affinity determination LV1050-Fc × 5C8var1-Fc for human PSMA and Vγ9Vδ2 TCR using biolayer interferometry

| Ligand | $K_D$ (M) | | $k_{on}$ (1/Ms) | | $k_{dis}$ (1/s) | |
| --- | --- | --- | --- | --- | --- | --- |
|  | mean | SD | $k_{on}$ (1/Ms) | SD | $k_{dis}$ (1/s) | SD |
| PSMA (n = 3) | 3.16E−08 | 1.24E−09 | 3.07E+05 | 7.41E+03 | 9.69E−03 | 4.73E−04 |
| Vγ9Vδ2 TCR (n = 4) | 6.35E−10 | 1.60E−10 | 2.40E+05 | 8.64E+03 | 1.51E−04 | 3.40E−05 |

TABLE 3

EC$_{50}$ values of Vγ9Vδ2-T cell degranulation and Vγ9Vδ2-T cell mediated tumor cell cytotoxicity with LV1050-Fc × 5C8var1-Fc in in vitro assays using Vγ9Vδ2-T cells and PSMA positive tumor cell lines

| Effector cells | Target cell line | Tested range (nM) | E:T ratio | Mean EC$_{50}$ (nM) (±SD) | Number of donors (n) and experiments |
|---|---|---|---|---|---|
| Degranulation after 4 hours | | | | | |
| Vγ9Vδ2-T cells | LNCaP | 3.2–0.000010 | 1:1 | 0.016 (0.0049) | n = 10 (10 donors in 5 exp) |
| Vγ9Vδ2-T cells | 22Rv1 | 3.2–0.000032 | 1:1 | 0.029 (0.0049) | n = 4 (4 donors in 2 exp) |
| Vγ9Vδ2-T cells | VCaP | 3.2–0.000032 | 1:1 | 0.028 (0.0064) | n = 4 (4 donors in 2 exp) |
| Cytotoxicity after 24 hours | | | | | |
| Vγ9Vδ2-T cells | LNCaP | 3.2–0.000010 | 1:1 | 0.017 (0.013) | n = 10 (10 donors in 7 exp, 4 donors tested twice) |
| Vγ9Vδ2-T cells | 22Rv1 | 3.2–0.000032 | 1:1 | 0.013 (0.0069) | n = 4 (4 donors in 2 exp) |
| Vγ9Vδ2-T cells | VCaP | 3.2–0.000032 | 1:1 | 0.015 (0.011) | n = 3 (3 donors in 2 exp) |

Next, the capacity of LV1050-Fc×5C8var1-Fc to induce target-dependent, Vγ9Vδ2-T cell-mediated tumor cell killing was determined in the same co-cultures at 24 hours, using a luminescence assay to quantify the release of an intracellular protease from dying/dead tumor cells (Cyto-Tox-Glo™ Cytotoxicity Assay, Promega). LV1050-Fc× 5C8var1-Fc induced strong, target-dependent and Vγ9Vδ2-T cell-mediated cytotoxicity of LNCaP, VCaP and 22Rv1 cells (FIG. 11B) with EC$_{50}$ values in the same range as for degranulation (Table 3).

Figure 11:
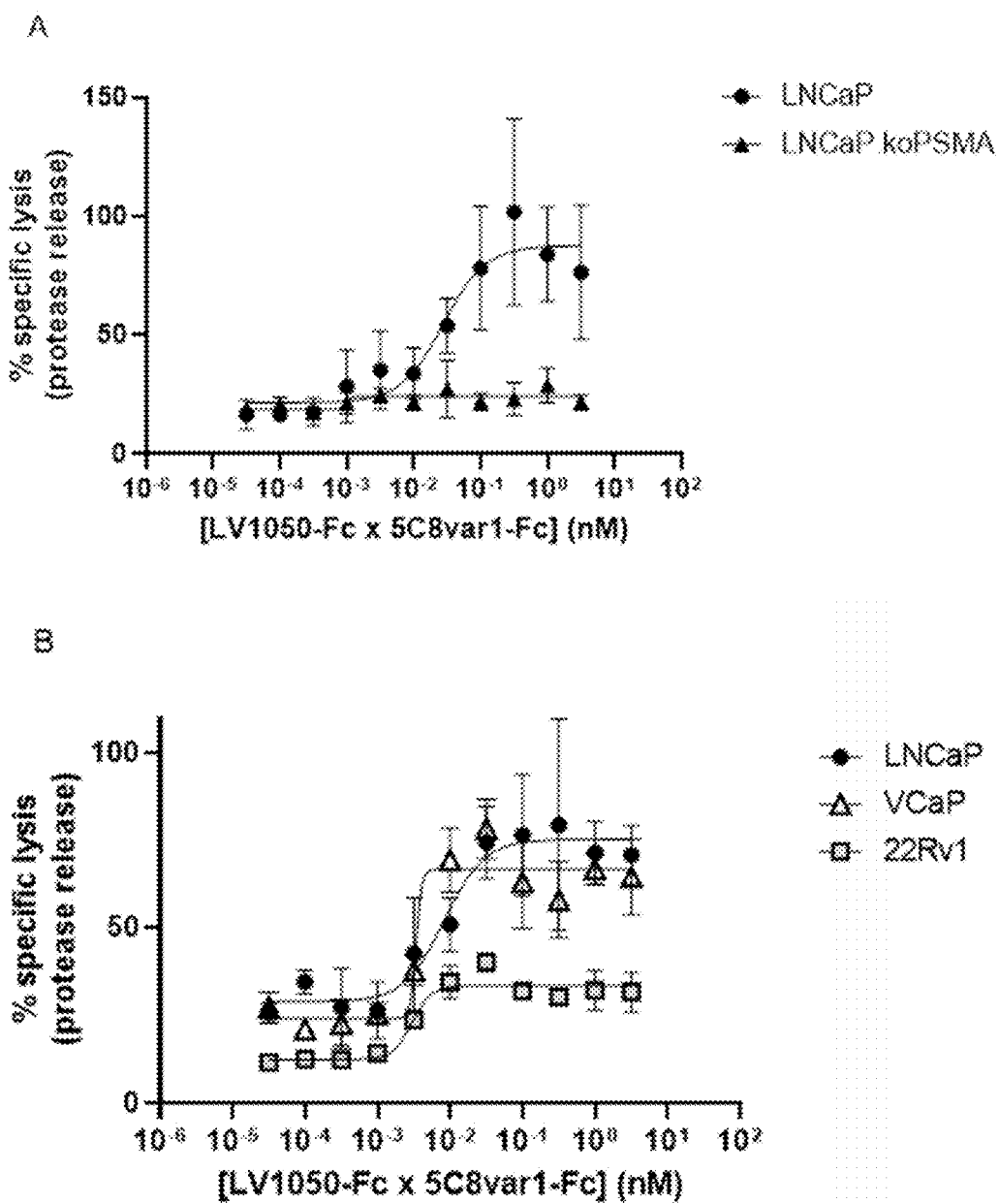
FIG. 11: Cytotoxicity assay using expanded Vγ9Vδ2-T cells and PSMA positive—or PSMA negative cells. Cytotoxicity was measured using primary, expanded Vγ9Vδ2-T cells cocultured with (A) LNCaP cells (PSMA-positive cells), versus LNCaP.koPSMA cells (PSMA-negative cells) or (B) different PSMA-expressing cell lines (LNCaP, 22Rv1 and VCaP cells). Cell death of target cells was determined by the activity in the medium of a defined intracellular protease using the CytoTox-Glo™ Assay.

In addition, Vγ9Vδ2-T cells were not activated by LV1050-Fc×5C8var1-Fc alone (in the absence of tumor cells), neither was lysis observed of tumor cells in which PSMA expression was abrogated (LNCaP.koPSMA) (FIG. 11A).

To study the effect of different E:T ratios on the potency of LV1050-Fc×5C8var1-Fc (concentration range tested: 10 fM to 3.2 nM), the number of target LNCaP cells was kept constant (i.e. 50,000) in a 24-hour cytotoxicity assay, while the number of effector Vγ9Vδ2-T cells was varied to obtain different E:T ratios (1:1, 1:10 and 1:100). As shown in Table 4, mean EC$_{50}$ values for Vγ9Vδ2-T cell-mediated cytotoxicity induced by LV1050-Fc×5C8var1-Fc were comparable between E:T ratio 1:1 and 1:10 (17±13 pM and 9.9±6.5 pM, respectively), while at the E:T ratio of 1:100, the level of cytotoxicity observed was too low to accurately calculate an EC$_{50}$ value. Even though the potency (EC$_{50}$) of LV1050-Fc×5C8var1-Fc in the assay was not affected, the maximum percentage of lysis observed was significantly lowered in the E:T ratio 1:10 compared to 1:1 E:T ratio (data not shown). Thus, the potency (i.e. EC$_{50}$ measured in the assay) of LV1050-Fc×5C8var1-Fc is not strongly affected by varying E:T ratios.

TABLE 4

EC$_{20}$, EC$_{50}$ and EC$_{90}$ values of Vγ9Vδ2-T cell cytotoxicity mediated by LV1050-Fc × 5C8var1-Fc using different E:T ratios.

| E:T ratio | Mean EC20 ± SD (pM) | Mean EC50 ± SD (pM) | Mean EC90 ± SD (pM) | Number of donors (n) and experiments |
|---|---|---|---|---|
| 1:1 | 4.3 ± 3.0 | 17 ± 13 | 79 ± 48 | n = 10 (10 donors in 7 expts, 4 donors tested twice) |
| 1:10 | 3.6 ± 1.3 | 9.9 ± 6.5 | 60 ± 59 | n = 4 (4 donors in 2 expts) |

Example 14: Functional Analysis of LV1050-Fc×5C8var1-Fc Using Patient-Derived Target Cells Patient-derived non-metastatic prostate cancer tissue was obtained and normal (non-malignant) and tumor tissue were processed as described in Example 9.

As a measure of activation of Vγ9Vδ2-T cells, upregulation of the degranulation marker CD107a (LAMP-1; detected using PE-labeled anti-human CD107a, Thermofisher) on Vγ9Vδ2-T cells present in the dissociated prostate samples (0.5–1×10$^5$ dissociated cells from normal (non-malignant) or primary tumor tissue) was determined in the presence or absence of 50 nM LV1050-Fc×5C8var1-Fc. After 4 hours, degranulation of Vγ9Vδ2-T cells was measured by CD107a expression and analyzed by a flow cytometry-based assay (determination of the percentage of EpCAM−/CD45+/CD3+/Vγ9+/Vδ2+/CD107a+ cells).

Also, the ability of LV1050-Fc×5C8var1-Fc to trigger degranulation of Vγ9Vδ2-T cells in autologous patient PMBC cultured in the presence of prostate tumor or normal (non-malignant) tissue was determined. To this aim, the same method as above was used, with the exception that here autologous PBMC were added at an effector to target (E:T; PBMC:prostate cell) ratio of 10:1 and incubated for 24 hours.

In dissociated prostate cancer tissue, but not in non-malignant prostate tissue, LV1050-Fc×5C8var1-Fc induced a statistically significant increase in degranulation of tissue infiltrating Vγ9Vδ2-T cells. A significantly higher percentage of CD107a-expressing Vγ9Vδ2-T cells was observed compared to incubation of tissue cells without the bispecific antibody (FIG. 12A). In normal tissue, LV1050-Fc× 5C8var1-Fc did not induce degranulation of tissue infiltrating Vγ9Vδ2-T cells (FIG. 12B).

In addition, the ability of LV1050-Fc×5C8var1-Fc to activate Vγ9Vδ2-T cells in autologous PMBC upon co-culture with patient prostate tumor or normal (non-malignant) tissue was determined. Co-culture in the presence of LV1050-Fc×5C8var1-Fc resulted in a significantly higher percentage of CD107a-expressing Vγ9Vδ2-T cells compared to incubation of tumor tissue cells and autologous PMBC alone (FIG. 13A). No activation of Vγ9Vδ2-T cells in autologous PBMC was observed when LV1050-Fc× 5C8var1-Fc was added to cultures of autologous PMBC and normal (non-malignant) prostate tissue (FIG. 13B).

Figure 14:
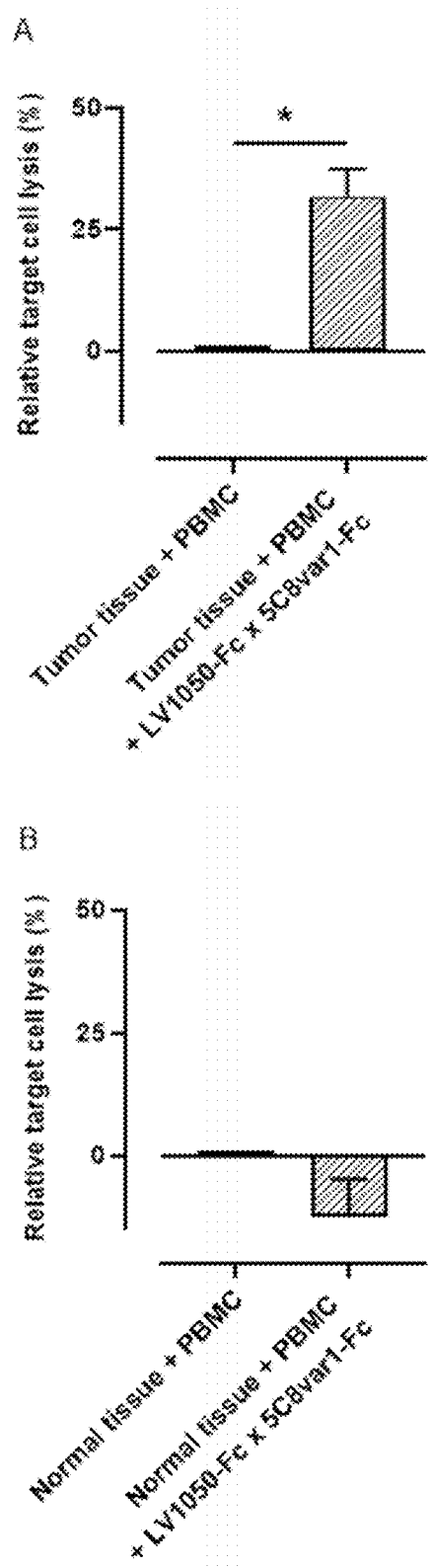
FIG. 14: Tumor cell lysis mediated by LV1050-Fc×5C8var1-Fc in the presence of autologous PBMC. Single cell suspensions from prostate tumor tissue (A) or normal (non-malignant) prostate tissue (B) were cultured with autologous PBMC in a 10:1 E:T ratio, with or without 50 nM of LV1050-Fc×5C8var1-Fc and incubated for 24 hours. Cytotoxicity was determined by flow cytometry using 7-AAD-exclusion, and expressed as the percentage of lysis relative to 'target cells plus PBMC'. Shown are mean and S.E.M (n=3), *$P<0.05$.

The specific cytotoxicity induced by LV1050-Fc× 5C8var1-Fc was tested in co-cultures of prostate tumor cells or normal (non-malignant) prostate cells and autologous PBMC as described in Example 10, except that an E:T ratio of 10:1 was used. LV1050-Fc×5C8var1-Fc induced statistically significant lysis of tumor cells in the presence of autologous PBMC, whereas normal (non-malignant) prostate cells were not lysed (FIG. 14).

Example 15: In Vivo Therapeutic Efficacy of LV1050-Fcx5C8var1-Fc

Immunodeficient NCG mice were subcutaneously inoculated with 5×10$^6$ 22Rv1 cells mixed with human PBMC in a 2:1 ratio (22Rv1:PBMC). PBMC from 2 donors showing different frequencies of Vγ9Vδ2-T cells in CD3+ T cells, donor #1 (21.9% Vγ9Vδ2-T cells) and donor #2 (8.8% Vγ9Vδ2-T cells), were used in this study. LV1050-Fcx 5C8var1-Fc (0.2 mg/kg or 2 mg/kg) or phosphate buffered saline (PBS) was administered IV every week (days 0, 7, 14 and 21) starting at the day of tumor cell—and PBMC inoculation. Tumor sizes were measured in two dimensions twice a week using a caliper. Mice were sacrificed when the mean tumor volume of a group exceeded 2,000 mm$^3$.

Figure 15:
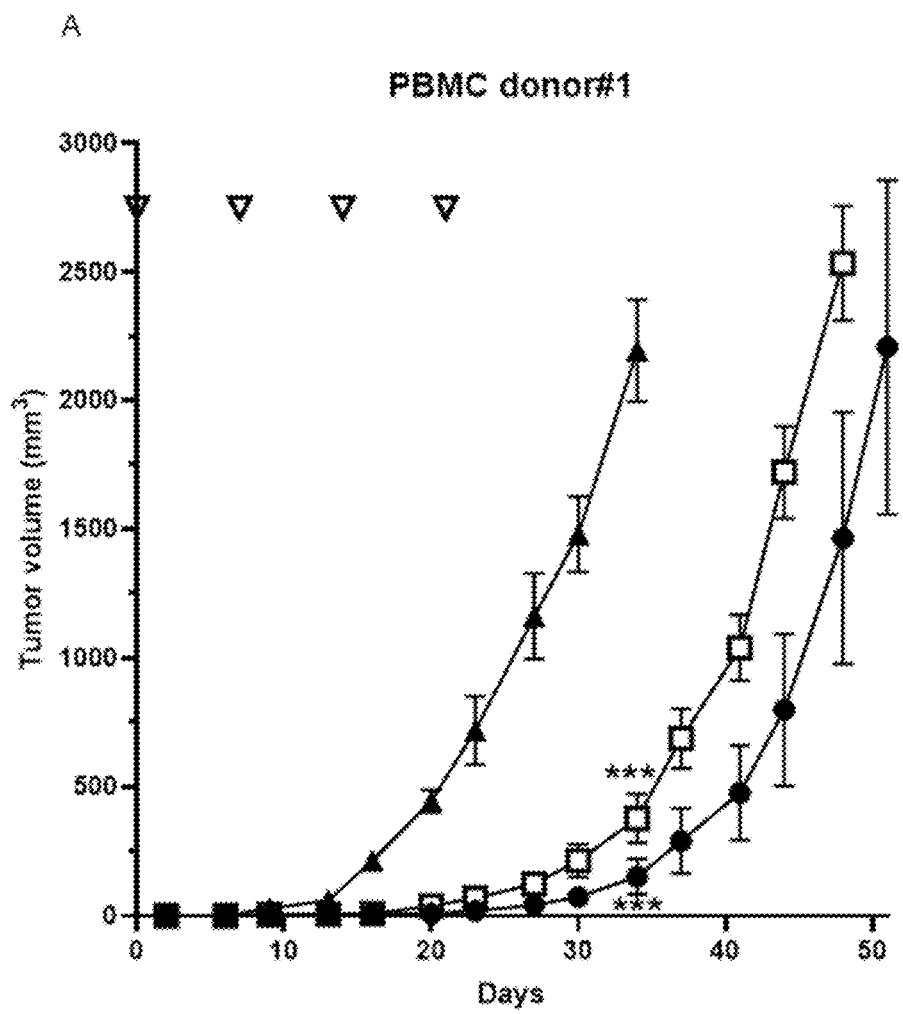
FIG. 15: The combination of LV1050-Fc×5C8var1-Fc and PBMC inhibits tumor growth in mice inoculated with 22Rv1 prostate carcinoma cells. NCG mice (n=4-6/group) were injected subcutaneously with 22Rv1 prostate cancer cells alone, or in combination with PBMC from two healthy donors. On days 0, 7, 14 and 21, LV1050-Fc×5C8var1-Fc (0.2 or 2 mg/kg) or PBS was injected IV. Twice a week, tumor sizes were measured using calipers. Mice were sacrificed when the mean tumor volume of a group exceeded 2,000 mm³. Tumor volumes (mm³; mean±SEM) are plotted as a function of the days after 22Rv1 prostate cancer cell inoculation. Statistical analysis (ANOVA (analysis of variance) with Dunnett's post hoc test) showed that using PBMC from donor#1, LV1050-Fc×5C8var1-Fc administered at 0.2 or 2 mg/kg resulted in a statistically significant reduction (***$P<0.001$) in the tumor growth rate, with TGI values on day 34 of 91% and 78% respectively. Using PBMC from donor #2, LV1050-Fc×5C8var1-Fc administered at 2 mg/kg resulted in a significant antitumor effect (*$P<0.01$), with a TGI value of 52% on day 41.
Figure 15:
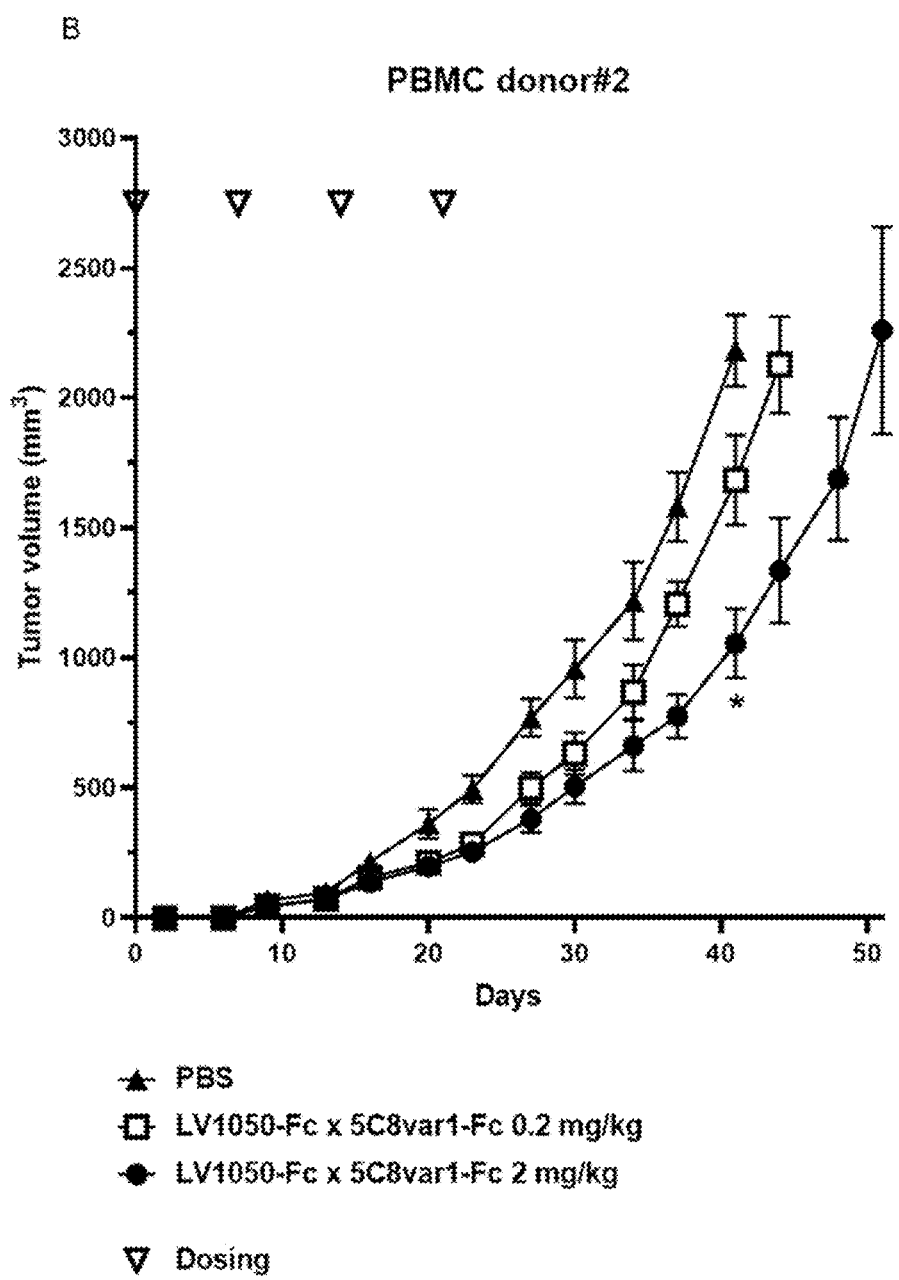

For mice injected with PBMC from donor #1, LV1050-Fcx5C8var1-Fc administration at 0.2 or 2 mg/kg resulted in statistically significant tumor growth inhibition (TGI) values of 91% and 78%, respectively, on day 34 (when mice in the control (PBS-treated) group were sacrificed: FIG. 15A). For mice injected with PBMC from donor #2, the TGI values observed on day 41 (when the mice in the corresponding PBS-treated group were sacrificed) were 23% and 52% for mice treated with 0.2 and 2 mg/kg of LV1050-Fcx5C8var1-Fc, respectively (FIG. 15B). For donor #2, statistical significance in TGI was found for the highest dose of the compound administered.

Example 16: Whole Blood Cytokine Release Evaluation

An in vitro cytokine release assay was performed using a solution phase assay employing fresh whole blood from 30 healthy donors. Different concentrations of LV1050-Fcx 5C8var1-Fc (ranging from 280 to 8.75 nM) were incubated for 24 hours with whole blood and the levels of seven cytokines (IL-2, IL-4, IL-6, IL-8, IL-10, IFN-γ and tumor necrosis factor (TNF)α) in plasma were measured using an immunoassay. Erbitux® (cetuximab) and Campath® (alemtuzumab) were included in the assay as control compounds inducing low and high cytokine release in the clinic, respectively. Staphylococcal enterotoxin B (SEB) was used as a positive assay control for the release of all the cytokines tested.

A summary of the results is shown in Table 5. LV1050-Fcx5C8var1-Fc only induced the release of IL-8 and IFN-γ. The LV1050-Fcx5C8var1-Fc-induced release of IL-8 was comparable to that induced by Erbitux®, an antibody that is known not to induce cytokine release syndrome (CRS) (or is known to induce low levels of cytokines) in patients. LV1050-Fcx5C8var1-Fc induced an IFN-γ release that was slightly higher when compared to Erbitux®, but the highest IFN-γ release observed was much lower than that induced by Campath®, an antibody clinically associated with CRS. Importantly, LV1050-Fcx5C8var1-Fc did not induce any IL-6 release, a prominent cytokine in CRS (Tanaka et al (2016) Immunotherapy 8: 959).

In an in vitro cytokine release assay where LV1050-Fcx 5C8var1-Fc was coated to high-binding 96 wells plates prior to incubation with fresh whole blood from 10 healthy donors, similar results were obtained. Here, LV1050-Fcx 5C8var1-Fc induced very low (median) levels of IL-6 and IL-8, which were comparable to the low response comparator, Erbitux® and no TNFα release was observed. LV1050-Fcx5C8var1-Fc induced higher (median) levels of IFN γ compared with Erbitux® at each concentration of the compound tested, yet median levels were substantially lower than that induced by Campath®.

TABLE 5

| Cytokine release profile (pg/mL) induced by LV1050-Fc × 5C8var1-Fc in fresh blood samples of healthy donors. | | | | | | | | |
|---|---|---|---|---|---|---|---|---|
| Test Article | | IL-2 | IL-4 | IL-6 | IL-8 | IL-10 | IFN-γ | TNFα |
| PBS (negative control) | | 0 | 0 | 0 | 0 | 0 | 0 | 0 |
| SEB (positive control) | | 24,470.9 | 53.3 | 5,613.2 | 8,936.3 | 1,010.3 | 61,792.2 | 4,302.2 |
| Erbitux ® | 280 nM | 0 | 0 | 0 | 15.1 | 0 | 0 | 0 |
| | 140 nM | 0 | 0 | 0 | 24.8 | 0 | 1.1 | 0 |
| | 70 nM | 0 | 0 | 4.7 | 15.6 | 0 | 0.5 | 0 |
| | 35 nM | 0 | 0 | 17.4 | 20.0 | 0 | 0 | 0 |
| | 17.5 nM | 0 | 0 | 46.0 | 16.6 | 0 | 0 | 0 |
| | 8.75 nM | 0 | 0 | 6.2 | 15.4 | 0 | 3.6 | 0 |
| Campath ® | 280 nM | 0 | 0 | 1,732.1 | 578.2 | 0.2 | 3,409.9 | 18.1 |
| | 140 nM | 0 | 0 | 1,360.3 | 392.7 | 0 | 4,029.0 | 12.9 |
| | 70 nM | 0 | 0 | 896.5 | 326.5 | 0 | 4,732.9 | 8.3 |
| | 35 nM | 0 | 0 | 714.9 | 255.5 | 0 | 5,313.4 | 14.5 |
| | 17.5 nM | 0 | 0 | 422.4 | 195.1 | 0 | 4,353.3 | 16.9 |
| | 8.75 nM | 0 | 0 | 400.9 | 180.5 | 0 | 4,932.2 | 20.6 |
| LV1050-Fc × 5C8var1-Fc | 280 nM | 0 | 0 | 0 | 35.4 | 0 | 9.4 | 0 |
| | 140 nM | 0 | 0 | 0 | 25.4 | 0 | 24.4 | 0 |
| | 70 nM | 0 | 0 | 0 | 24.2 | 0 | 37.9 | 0 |
| | 35 nM | 0 | 0 | 0 | 20.3 | 0 | 49.6 | 0 |
| | 17.5 nM | 0 | 0 | 0 | 28.2 | 0 | 50.0 | 0 |
| | 8.75 nM* | 0 | 0 | 0 | 19.2 | 0 | 81.4 | 0 |

Median cytokine levels (pg/mL) for each drug/dose combination measured in fresh blood samples of 30 healthy donors by an in vitro cytokine release assay.

Example 17: Pharmacokinetics

LV1050-Fcx5C8var1-Fc contains a human Fc domain, which is expected to extend the in vivo half-life of the compound by binding to the human FcRn receptor. To verify this, LV1050-Fcx5C8var1-Fc was co-administered with a human IgG control in three single IV doses of 2 mg/kg, 5 mg/kg and 10 mg/kg in human FcRn Tg32 SCID mice (Jackson labs: JAX). Blood samples were collected at different time points (5 m, 8 h, 1, 3, 7, 10, 14, 17, 21 and 28 days) after administration and concentrations of LV1050-Fcx5C8var1-Fc were assessed using an antigen capture ELISA. The results obtained in this model system show that LV1050-Fcx5C8var1-Fc has a half-life in these transgenic mice that ranges between 140 and 172 hours (5.8-7.2 days, FIG. 16), comparable to the half-life that an IgG-based antibody has in this system.

Figure 17:
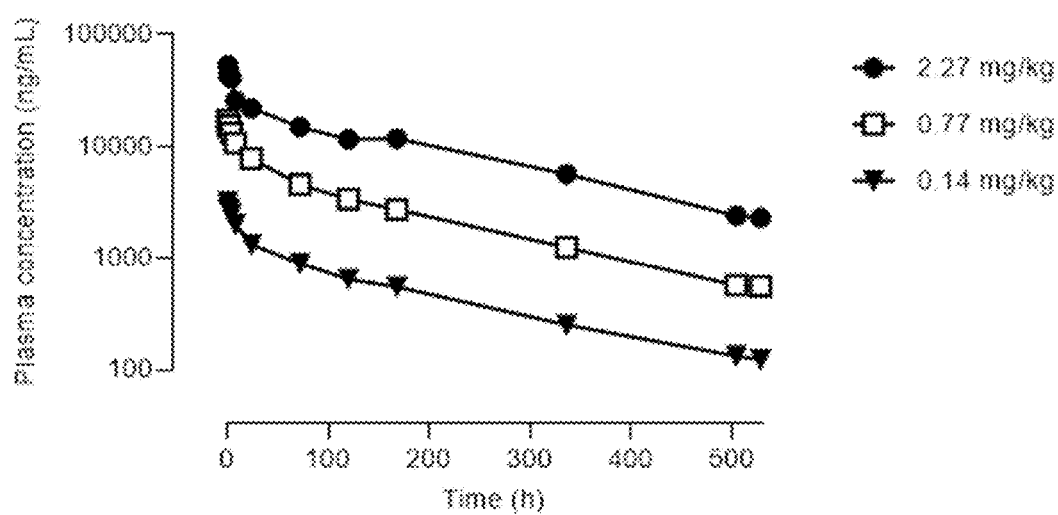
FIG. 17: Pharmacokinetics of different doses of LV1050-Fc×5C8var1-Fc in NHP after a single IV dose. Plasma concentrations of LV1050-Fc×5C8var1-Fc were measured pre-dose and then at 0.5, 1, 2, 4, 8, 24, 72, 120, 168, 336, 504 and 528 hours after administration. The plasma concentration of LV1050-Fc×5C8var1 (Y-axis) is given as a function of time.

The pharmacokinetics of LV1050-Fcx5C8var1-Fc were also evaluated in non-human primates (NHP). Three female cynomolgus monkeys were given a single IV dose of LV1050-Fcx5C8var1-Fc (0.14, 0.77 and 2.27 mg/kg (1 animal per dose)) using a 30-minute IV infusion. The half-life of LV1050-Fcx5C8var1-Fc ranged between 150 and 166 hours (6.3-6.9 days) (FIG. 17), which is in line with the half-lives of IgG-based humanized antibodies which do not bind to the cynomolgus ortholog targets (Walker et al. (2019) PLOS ONE 14: e0217061). A dose-proportional increase in exposure was observed. The pharmacokinetic parameters are provided in Table 6.

TABLE 7

Results of SE-HPLC for clone pools obtained by transfection of different ratios of expression vectors containing LV1050-Fc or 5C8var1-Fc.

| | | rel. peak areas [%] | | |
|---|---|---|---|---|
| Pool-ID. | Ratio LV1050-Fc:5c8var1-Fc | HMW Species | Main | LMW species |
| DGC8-T1P | 1:1 | 4.1 | 95.8 | 0.0 |
| DGC8-T3P | 1:1.25 | 4.5 | 94.1 | 1.4 |
| DGC8-T5P | 1:1.5 | 4.3 | 93.2 | 2.5 |
| DGC8-T7P | 1.25:1 | 3.6 | 96.4 | 0.1 |
| DGC8-T9P | 1.5:1 | 3.6 | 96.3 | 0.0 |

HMW—high molecular weight;
LMW—low molecular weight

TABLE 6

Pharmacokinetic parameters of LV1050-Fc × 5C8var1-Fc in cynomolgus monkeys after a single IV dose.

| Animal ID | Adm. dose (mg/kg) | $T_{max}$ (hrs) | $C_{max}$ (mg/mL) | $nC_{max}$ (mg/mL)/ (mg/kg) | $T_{1/2}$ (hrs) | $AUC_{0-\infty}$ (mg · h/mL) | $nAUC_{0-\infty}$ (mg · h/mL)/ (mg/kg) | Cl (mL/h/kg) | Vz (mL/kg) |
|---|---|---|---|---|---|---|---|---|---|
| 61 | 0.14 | 1 | 3.17 | 22.6 | 162.1 | 297.9 | 2127.9 | 0.47 | 109.9 |
| 62 | 0.77 | 1 | 17.1 | 22.2 | 150.0 | 1513.2 | 1965.2 | 0.51 | 110.1 |
| 63 | 2.27 | 1 | 53.6 | 23.6 | 165.9 | 5548.7 | 2444.4 | 0.41 | 97.9 |

CL = clearance;
(n)$C_{max}$ = (normalized) maximum concentration after dosing;
(n)$AUC_\infty$ = (normalized) area under the concentration versus time curve from time-point t = 0 h to infinity;
$T_{max}$ = the time after dosing at which the maximum concentration reached;
$t_{1/2}$ = elimination half-life;
$V_z$ = apparent volume of distribution.

Example 18: Homogeneous Product Irrespective of Transfection Ratio cDNAs encoding the relevant two antibody heavy chains of LV1050-Fcx5C8var1-Fc were each cloned in expression vectors suitable for manufacturing. Different ratio's, 1:1, 1:1.25, 1:1.5, 1.25:1 and 1.5:1, of expression vectors containing LV1050-Fc or 5C8var1-Fc were used for transfection of cells suitable for manufacturing. Cells were then selected for resistance to two different antibiotics and antibodies were produced from selected cell pools by means of fed batch production. Size Exclusion High Performance Liquid Chromatography (SE-HPLC) analysis of the produced antibodies revealed high product purities (dimer content): between 93.2% and 96.4% of the secreted protein was at the expected molecular seize, irrespective of the transfection ratio (main peak area in Table 7). Reverse Phase HPLCd (RP-HPLC) analysis was established to further distinguish the monomers (LV1050-Fc and 5C8var1-Fc) and homodimers (LV1050-FcxLV1050-Fc and 5C8var1-Fcx 5C8var1-Fc) from intended LAVA heterodimers (LV1050-Fcx5C8var1-Fc). All clone pool samples revealed a high content of intended heterodimer LAVA LV1050-Fcx 5C8var1-Fc between 86.1 and 94.9%. Clone pools DGC8-T1P, -T3P and -T5P revealed an elevated percentage of 5C8var1-Fcx5C8var1-Fc dimer.

Example 19: Formulation of LV1050-Fcx5C8var1-Fc

From a selected cell clone, LV1050-Fcx5C8var1-Fc product was obtained by means of production in a bioreactor system, and after harvest and purification formulated at protein concentrations of 0.5 mg/mL and 10 mg/mL using four types of formulation buffers:

| Buffer | Formulation |
|---|---|
| Buffer 1 | 10 mM Histidine + 280 mM Sucrose + 0.02% Polysorbate 80, pH 6.0 |
| Buffer 2 | 10 mM Histidine + 280 mM Sucrose + 0.02% Polysorbate 80, pH 6.0 + 1 mM Methionine |
| Buffer 3 | 10 mM Sodium acetate + 280 mM Sucrose + 0.02% Polysorbate 80, pH 5.5 |
| Buffer 4 | 10 mM Sodium acetate + 280 mM Sucrose + 0.02% Polysorbate 80, pH 5.5 + 1 mM Methionine |

Formulated samples were subjected to several storage conditions (defined below), for up to 12 weeks. Additionally, several stress tests were applied:
 (a) Storage at 5° C.±3° C.
 (b) Storage at −80° C.±10° C.
 (c) Accelerated storage conditions at 25° C.±2° C./60% relative humidity (RH)±5%
 (d) Heat stress at 40° C.±2° C./75% RH±5%
 (e) Freeze/Thaw cycles: The samples were completely frozen to −80±10° C. Subsequently, five freeze/thaw cycles have been performed after allowing samples to completely thaw at room temperature (15-25° C.).

(f) Agitation stress: Samples agitated at 240 rpm for 7 days at room temperature (EP15° C.-25° C.).

(g) Oxidation: The samples were spiked with 0.01% (v/v) hydrogen peroxide (H2O2) and incubated for 7 days at 25° C.±2° C./60% RH±5%.

(h) Photostability: >1.2 million lux hours and >200 watt hours/square meter of near ultra violet energy were applied at 25° C.±2° C./60% RH±5%.

Initial (=t0) 5° C.±3° C. samples served as a reference. Samples were analyzed using the following analytical methods:

| Method | Assessment |
| --- | --- |
| Clarity | Appearance |
| Color | Appearance |
| pH | pH |
| $A_{280}$ (UV/VIS) | Content |
| Stray light | Integrity |
| SE-HPLC | Integrity |
| Cation-exchange (CIEX)-HPLC | Integrity |
| Capillary electrophoresis sodium dodecyl sulfate (CE-SDS_(non-reduced) | Integrity |
| CE-SDS (reduced) | Integrity |
| Activity assay-PSMA binding ELISA | Potency |
| Peptide mapping | Identity |
| Differential scanning | Integrity |
| Liquid chromatography-mass spectrometry (LC-MS) (oxidation) | Integrity |

The results of the stability over time study were highly comparable for Clarity, Color, pH, $A_{280}$ (UV-VIS), Stray light, SE-HPLC, CIEX-HPLC, CE-SDS and PSMA binding, Differential Scanning and Peptide Fingerprint for storage temperatures at −80° C.±10° C., 5° C.±3° C. and 25° C.±2° C./60% RH±5%. The results of the measurements indicate that the product was highly stable with the chosen buffer conditions and only slight effects were observed over time.

Distinct effects were detected under stress conditions at 40° C.±2° C./75% RH±5% particularly at five weeks, enabling a differentiation between the tested buffers and concentrations. The CIEX-HPLC analyses of samples kept at 40° C.±2° C./75% RH±5% and 5 weeks showed that at this timepoint the content of main variant dropped below 60% for all tested buffers and product concentrations. In the histidine-based formulation a slightly lower decrease was observed in main variant percentage compared to the acetate-based formulation.

The CE-SDS results revealed that storage over time at 40° C. resulted in a slight increase of LMW species of the product up to 5%. This effect was slightly more pronounced for the 10 mg/mL samples in buffer 1 and 3. Nevertheless, the antibody was found very stable, even under strong stress conditions as 40° C.±2° C./75% RH±5% for 5 weeks.

PSMA binding data for the 5 weeks' time point at 40° C.±2° C./75% RH±5% showed a strong increase in the $EC_{50}$ for 10 mg/mL samples in buffer 1 and 3. The increase in the $EC_{50}$ measured in the PSMA binding assay correlated with the slight increase in the relative HMW species amount observed in the SE-HPLC analysis from 0.3 and 0.2% to 0.6 and 0.7%, respectively.

The results from the stress tests (freeze/thawing (five F/T cycles), photo-, agitation- and oxidation stress) showed a different ranking than the temperature stability study. In the temperature stability study, 10 mg/ml samples in buffer 3 showed the highest amounts of results outside their predefined analytical threshold, whereas the stress stability study revealed increased results outside their predefined analytical threshold for 0.5 mg/mL samples in buffer 1 compared to the other conditions.

LC-MS analysis revealed that the addition of methionine (present in buffer 2 and buffer 4) to prevent oxidation of the product was effective.

In conclusion, LV1050-Fc×5C8var1-Fc was most stable when formulated in buffer 2 and buffer 4. An overview of the sum of results outside their predefined analytical threshold for temperature stability, stress stability and overall stability (temperature plus stress) is shown in Table 8.

For final formulation, 10 mM Histidine+280 mM Sucrose+0.02% Polysorbate 80, pH 6.0+1 mM Methionine was chosen, at a protein concentration between 0.5 and 10 mg/mL.

TABLE 8

Sum of results outside their predefined analytical threshold for temperature stability, stress stability and overall stability (temperature plus stress).

| Buffer | Buffer 1 | | Buffer 2 | | Buffer 3 | | Buffer 4 | |
| --- | --- | --- | --- | --- | --- | --- | --- | --- |
| Protein conc. (mg/mL) | 0.5 | 10 | 0.5 | 10 | 0.5 | 10 | 0.5 | 10 |
| Temperature stability | 0 | 2 | 0 | 0 | 1 | 6 | 0 | 0 |
| Stress stability | 11 | 5 | 5 | 4 | 5 | 5 | 5 | 4 |
| Overall stability | 11 | 7 | 5 | 4 | 6 | 11 | 5 | 4 |

The invention claimed is:

1. A bispecific antibody, comprising (a) a first polypeptide comprising SEQ ID NO: 26; and
(b) a second polypeptide comprising SEQ ID NO: 25.

2. A nucleic acid construct encoding the bispecific antibody of claim 1.

3. An expression vector comprising the polynucleotide nucleic acid construct of claim 2.

4. A pharmaceutical composition comprising the bispecific antibody of claim 1 and a pharmaceutically acceptable excipient.

5. A method of treating a cancer in a subject in need thereof comprising administering the bispecific antibody of claim 1.

6. The method according to claim 5, wherein the cancer is a prostate cancer, a colorectal cancer, a lung cancer, a breast cancer, an endometrial and ovarian cancer, a gastric cancer, a renal cell cancer, an urothelial cancer, a hepatocellular cancer, an oral squamous cancer, a thyroid tumor, an adenoid cystic carcinoma, or a glioblastoma.

7. The method according to claim 6, wherein the prostate cancer is metastatic or non-metastatic prostate cancer.

8. The method according to claim 5, further comprising administering an additional therapeutic agent.

* * * * *